US007317801B1

(12) United States Patent
Amir

(10) Patent No.: US 7,317,801 B1
(45) Date of Patent: Jan. 8, 2008

(54) ACTIVE ACOUSTIC NOISE REDUCTION SYSTEM

(75) Inventor: Nehemia Amir, Rishon Lezion (IL)

(73) Assignee: Silentium Ltd, Rehovol (IL)

( * ) Notice: Subject to any disclaimer, the term of this patent is extended or adjusted under 35 U.S.C. 154(b) by 0 days.

(21) Appl. No.: 09/120,973

(22) Filed: Jul. 22, 1998

(30) Foreign Application Priority Data

Aug. 14, 1997 (IL) ..................................... 121555

(51) Int. Cl.
*A61F 11/06* (2006.01)
*G10K 11/16* (2006.01)
*H03B 29/00* (2006.01)
*H04B 15/00* (2006.01)

(52) U.S. Cl. ................... 381/71.1; 381/94.7; 381/71.8; 379/406.05

(58) Field of Classification Search ............... 381/71.1, 381/71.2, 94.1, 94.8, 86, 95–96, 83, 93, 56–58, 381/71.14; 379/406.01, 406.05, 406.08
See application file for complete search history.

(56) References Cited

U.S. PATENT DOCUMENTS 4,025,724 A * 5/1977 Davidson et al. .......... 381/71.2
4,965,832 A 10/1990 Edwards et al.
5,182,774 A * 1/1993 Bourk ....................... 381/71.6
5,271,062 A 12/1993 Sugita et al.
5,347,586 A 9/1994 Hill et al.
5,365,594 A 11/1994 Ross et al.
5,410,607 A 4/1995 Mason et al.
5,471,537 A 11/1995 Castwall
5,475,731 A * 12/1995 Rasmusson ................. 379/406
5,519,637 A 5/1996 Mathur et al.
5,553,154 A 9/1996 Tamamura et al.
5,602,927 A * 2/1997 Tamamura et al. ........ 381/71.4
5,613,009 A 3/1997 Miyazaki et al.

(Continued)

FOREIGN PATENT DOCUMENTS

EP 0759606 2/1997

(Continued)

OTHER PUBLICATIONS

Copy of International Search Report for EP 02 02 3483, mailed on Apr. 8, 2003.

*Primary Examiner*—Xu Mei
(74) *Attorney, Agent, or Firm*—EMPK & Shiloh, LLP

(57) ABSTRACT

An active acoustic noise reduction system which comprises a single input transducer and an output actuator that are physically located next to each other in the same location. In one embodiment, the input transducer and the output actuator are a hybrid represented by a single element. The active noise reduction system is located as close as possible to the noise source and functions to generate an antinoise cancellation sound wave with minimum delay and opposite phase with respect to the noise source. The noise reduction system also comprises a non linearity correction circuit, a delayed cancellation circuit and variable gain amplifier. The system provides user control of the quiet zones generated by the system by varying the gain of the variable gain amplifier. The system provides a user with the ability In one embodiment, an echo canceler is utilized to remove echoes fed back from the output actuator. In another embodiment, an input decoder is used instead of an echo canceler to remove feedback picked up from the output actuator.

4 Claims, 14 Drawing Sheets

U.S. PATENT DOCUMENTS

| | | | | | |
|---|---|---|---|---|---|
| 5,618,010 | A | | 4/1997 | Pla et al. | |
| 5,627,896 | A | | 5/1997 | Southward et al. | |
| 5,680,393 | A | * | 10/1997 | Bourmeyster et al. | 370/286 |
| 5,680,450 | A | * | 10/1997 | Dent et al. | 379/406 |
| 5,745,731 | A | * | 4/1998 | Kim et al. | 711/149 |
| 5,748,749 | A | | 5/1998 | Miller et al. | |
| 5,768,398 | A | * | 6/1998 | Janse et al. | 381/103 |
| 6,160,892 | A | | 12/2000 | Ver | |
| 6,181,753 | B1 | * | 1/2001 | Takada et al. | 375/346 |
| 6,351,532 | B1 | | 2/2002 | Takada et al. | |
| 6,535,609 | B1 | * | 3/2003 | Finn et al. | 381/86 |

FOREIGN PATENT DOCUMENTS

| | | |
|---|---|---|
| EP | 0818771 | 1/1998 |
| EP | 0903726 | 3/1999 |
| WO | WO 02/32356 | 4/2002 |

* cited by examiner

170

ACTIVE ACOUSTIC NOISE REDUCTION SYSTEM

CROSS-REFERENCE TO RELATED APPLICATIONS

This application claims priority of Israeli Patent Application No. 121555, filed on Aug. 14, 1997.

FIELD OF THE INVENTION

The present invention relates generally to noise reduction systems and more particularly relates to acoustic noise reduction systems adapted to reduce the noise at a point relatively far from the noise source.

BACKGROUND OF THE INVENTION

Digital adaptive reduction of noise in the time domain is typically performed by sampling the analog output of a microphone that is appropriately positioned to sense the input noise. The sampled analog noise is then converted to digital format via an A/D converter, passed through an adaptive digital filter and then converted back to analog via a D/A converter before being output to a speaker. The analog output of a microphone is utilized as the input to the internal adaptive algorithm within the prior art noise reduction system.

Since the group delay of such a system as described above is relatively large, a typical method of noise reduction employed in the prior art using such a system is to reduce the effect of periodic noise sources as opposed to arbitrary noise sources.

Typical prior art noise reduction systems utilize an adaptive digital filter in the main data path to reduce the effect of the noise source. This causes the group delay of the system to be relatively large.

For example, U.S. Pat. No. 5,553,154, issued to Tamamura et al., discloses an adaptive filter that receives pulses that are synchronized with the period of the noise. The interval of the input noise determines the length of the taps in the delay line of the adaptive filter.

U.S. Pat. No. 5,613,009, issued to Miyazaki et al., discloses a vibration control system that a reference signal from the vibration source and an error signal from an object are input to the adaptive filter. Feedback means generates a feedback control signal in combination with a feedfoward signal, forms a drive signal for a vibrating means.

U.S. Pat. No. 5,627,896, issued to Southward et al., discloses an active system for controlling noise. The system operates by limiting the output gain from a gradient descent algorithm.

Frequency domain analysis of the input data in the main data path of the system is another common technique utilized by prior art noise reduction systems. For example, U.S. Pat. No. 5,271,062, issued to Sugita et al., discloses a noise reduction system that generates a signal having the same frequency but inverted phase relative to the input noise.

U.S. Pat. No. 5,347,586, issued to Hill et al., discloses a noise control system comprising a reference microphone for generating a reference signal that is correlated with the noise emanating a noise source, a plurality of loudspeakers, a plurality of error microphones for generating a plurality of error signals and an adaptive controller.

U.S. Pat. No. 5,365,594, issued to Ross et al., discloses a vibration control system that utilizes a vibration input signal derived from a sensor sampling the vibrations to generate an output representative of the interference free vibration of a primary source.

U.S. Pat. No. 5,519,637, issued to Mthur et al., discloses an active structural acoustic control method for reducing the sound emitted through a structure. The method uses an array of transducers placed in a far field structure and an array of actuators mounted or embedded in that structure. Each is controlled by the system controller and uses reference signals derived from the noise source.

Alternatively, another method of noise cancellation used in prior art systems places the microphone as close to the noise source as possible and the loudspeaker relatively far from the microphone so as to create a delay equal to the time for the noise to travel from the microphone to the speaker. This delay is intentionally created in order to match the internal signal processing time of the noise reduction system. The propagation time for the noise is configured to roughly match and compensate for the signal propagation time within the noise reduction system. This noise reduction method is particularly useful for cancellation of noise in a duct such as an air conditioning duct. The internal signal processing is performed during the time that it takes for the sound waves to travel from the microphone to the loudspeaker.

Another prior art noise reduction technique related to the one just described, is to place the speaker close the noise source rather than far away from it, place a second microphone in the desired quiet zone and to adapt a digital filter utilizing the second microphone output. However, this method is useful for canceling repetitive noise only.

The implementation and calibration of noise reduction systems made according to the prior art techniques described above are typically very difficult and correspondingly costly due to the need to supply a plurality of different elements, e.g., two microphones and a loudspeaker, and place these plurality of elements in their appropriate places.

Another disadvantage of prior art noise reduction systems is that if the canceled noise is not periodic in nature, then the physical dimensions of the cancellation system become relatively large. When the loudspeaker is located far away from the noise source, then the noise cancellation is localized and limited to a relatively small area. It would thus be desirable to have a noise reduction system in which the physical design and calibration limitations of prior art noise reduction systems are avoided.

U.S. Pat. No. 5,410,607, issued to Mason et al., discloses a noise cancellation system for reducing noise radiated from a complex vibrating surface. The system includes a motion sensor, a controller having fixed transfer function and operative to generate an antinoise signal, and an acoustic driver operative to generate an acoustic antinoise field that is substantially 180 degrees out of phase with the original noise field. The antinoise field reduces the original noise field using destructive interference.

U.S. Pat. No. 5,618,010, issued to Pla et al., discloses an active noise reduction system that utilizes a noise radiating panel to generate a noise that cancels the noise source. A piezoceramic actuator is connected to the panel. A sensing device such as an accelerometer is used in generating an opposite noise signal with which to cancel the noise source in the vicinity of the panel.

SUMMARY OF THE INVENTION

The present invention is an active acoustic noise reduction system which comprises an input transducer and an output actuator that are physically located next to each other in the same location. In one embodiment, the input transducer and the output actuator are a hybrid represented by a single element. The active noise reduction system is located as close as possible to the noise source and functions to generate the cancellation sound wave with minimum delay with respect to the noise source.

The active noise reduction system, located very close to the noise source, functions to generate synthetic sound waves having a phase opposite that the noise. Both the noise source and the active noise reduction system might be situated within an enclosure or may be situated external to an enclosure. In one embodiment of the invention, the noise sound wave and the cancellation sound wave spread almost from the same point producing a high amount of noise cancellation. The output power of the cancellation signal is chosen so as to achieve maximum cancellation of the noise sound.

Another embodiment of the invention is applicable when it is possible to place the noise reduction system very close to the noise source but the noise source body is much larger then the noise cancellation system. In the case when the noise body generates noise having the same phase in a direction towards the noise reduction system, good cancellation is achieved in the far field. Another benefit is that the noise cancellation is based on detecting the noise at only one point on the noise source body.

Another embodiment of the invention is applicable when it is not possible to get close to the noise sound source or when the noise does not emanate from a single point or when the noise source body is relatively large compared to the system. In this case, a plurality of noise reduction systems are placed side by side, i.e., in an array configuration, to produce a 'wall of silence' with each noise reduction system generating cancellation sound waves in accordance with the noise detected at that particular point. Each element of the noise reduction array in this case operate independently of each other as opposed to each element being connected to some central processing unit.

In another embodiment of the invention, the noise cancellation system is utilized as a speaker or sound generating device for multimedia sources. In this mode, the noise cancellation system not only serves to perform noise cancellation, but also serves to generate meaningful sound. In other words, the system can function to both remove unwanted noise and intentionally insert sound such as music, thus replacing noise with music. This functions to reduce the annoyance of background noise by adding pleasant sounding music, for example.

The acoustic cancellation method of the present invention is based on the behavior of acoustic beam patterns in air. Cancellation of the noise is achieved in an area far from the noise source while in an area relatively close to the noise source there may be pockets of noise that exist. The length of the quiet zone, as measured from the noise source, is determined by the power of the cancellation signal generated and output by the system. Since the output acoustic beam pattern is dependent on the characteristics of the output actuator and on the main cancellation frequency that is used, the type of output actuator or the angle between a plurality of actuators may need to be varied in order to achieve optimum results for different noise frequencies. The noise reduction method of the present invention is capable of achieving effective cancellation of the noise when the surface of the noise source is complex given that the distance from the noise source to the point of cancellation is bigger then the length of the noise source itself.

In addition to sensing sound from the noise source, the system also detects the sound from the output actuator. The portion of the input signal that is due to the output actuator is removed using an echo cancellation technique. If the output and input transducers are acoustically separate elements and there exists acoustic delayed feedback in the system, then using an echo cancellation system is preferred. Another advantage of the echo cancellation system is the elimination of feedback sound emanating from walls, furniture, etc. and sensed by the input transducer. If there is no delayed time feedback from the output transducer to the input transducer and a directional input transducer is used, then a computation may be performed on the input signal, instead of using an echo cancellation system, to discern the actual noise signal from the input signal.

In addition, the cancellation signal generated by the output actuator may be reflected from the noise source itself thus adding to the amount of noise present. In order to eliminate this type of noise, a delayed cancellation signal is generated by the system. The delay and phase shift applied to the cancellation signal is matched to the delay and phase shift associated with the reflection and feedback of the sound from the output actuator.

There is therefore provided in accordance with the present invention an acoustic noise reduction system for reducing the effects of a noise source, comprising input transducer means for sensing the acoustic noise field generated by the noise source and for generating an input signal therefrom, output actuator means for generating an acoustic output field that is effective to reduce the level of the acoustic noise field, correction means for adjusting the input signal generated by the input transducer to compensate for the non linear characteristics of the input transducer and output actuator, echo cancellation means for removing from the input signal a portion of the output of the output actuator means fed back through the input transducer means, the output of the echo cancellation means representing a signal corresponding to substantially the noise source by itself, antinoise means for generating an antinoise signal opposite in phase to the input signal, the output actuator means generating the acoustic output field from the antinoise signal and wherein the input transducer means is located in relatively close proximity to the output actuator means.

There is also provided in accordance with the present invention an acoustic noise reduction system for reducing the effects of a noise source, comprising input transducer means for sensing the acoustic noise field generated by the noise source and for generating an input signal therefrom, output actuator means for generating an acoustic output field that is effective to reduce the level of the acoustic noise field, correction means for adjusting the input signal generated by the input transducer to compensate for the non linear characteristics of the input transducer, input decoding means for removing extraneous signals from the input signal so as to generate a signal corresponding to substantially the noise source alone, antinoise means for generating an antinoise signal opposite in phase to the input signal, the output actuator means generating the acoustic output field from the antinoise signal and wherein the input transducer means is located in relatively close proximity to the output actuator means.

The correction means comprising storage means for storing a plurality of coefficients, coefficient processing means for dynamically updating the values of the plurality of coefficients stored in the storage means and means for generating a corrected input signal from the contents of the storage means and the input signal.

The correction means comprising storage means for storing a plurality of coefficients, sigma generating means for outputting a signal corresponding to substantially the noise source only, coefficient processing means for dynamically updating the values of the plurality of coefficients stored in the storage means and means for generating a corrected input signal from the contents of the storage means and the input signal.

The echo cancellation means comprises a digital filter having a delay line with a number of taps whose total delay time is equivalent to at least a system time delay of the noise reduction system, adaptation means for dynamically adjusting the coefficient values associated with each of the taps of the digital filter and summing means for adding the output of the digital filter with the output of the correction means.

The antinoise means comprises a variable gain amplifier operative to generate an amplified signal 180 degrees opposite in phase from the input signal and gain control means for dynamically controlling the gain of the variable gain amplifier. The gain control means is adapted to receive a manual input control signal from a user which determines the gain of the variable gain amplifier, the user able to vary the location of a quiet zone generated by the system by varying the input control signal. The input control signal is generated by the user remotely from the system and transmitted to the system via wireless communication means.

The system further comprises a low pass filter operative to reduce oscillations present in the system derived from feedback of the acoustic output field to the input transducer. Also, the system further comprises delay cancellation means for reducing the effect of echo signals caused by the antinoise means sensed by the input transducer. The delay cancellation means comprises a plurality of delay cancellation circuits wherein each delay cancellation circuit is operative to reduce the effect of the echo caused by previous delay cancellation circuits.

Further, there is provided in accordance with the present invention a method for reducing the effects of a noise source, comprising the steps of sensing the acoustic noise field generated by the noise source and generating an input signal therefrom, generating an acoustic output field that is effective to reduce the level of the acoustic noise field, adjusting the input signal generated by an input transducer to compensate for the non linear characteristics of the input transducer and an output actuator, removing from the input signal a portion of the output of the output actuator fed back through the input transducer, generating a signal corresponding to substantially the noise source by itself and generating an antinoise signal opposite in phase to the input signal, generating the acoustic output field from the antinoise signal.

Also, there is provided in accordance with the present invention a method for reducing the effects of a noise source, comprising the steps of sensing the acoustic noise field generated by the noise source and for generating an input signal therefrom, generating an acoustic output field that is effective to reduce the level of the acoustic noise field, adjusting the input signal generated by an input transducer to compensate for the non linear characteristics of the input transducer, removing extraneous signals from the input signal so as to generate a signal corresponding to substantially the noise source alone and generating an antinoise signal opposite in phase to the input signal, the output actuator means generating the acoustic output field from the antinoise signal.

BRIEF DESCRIPTION OF THE DRAWINGS

The invention is herein described, by way of example only, with reference to the accompanying drawings, wherein.

DETAILED DESCRIPTION OF THE INVENTION

Figure 1:
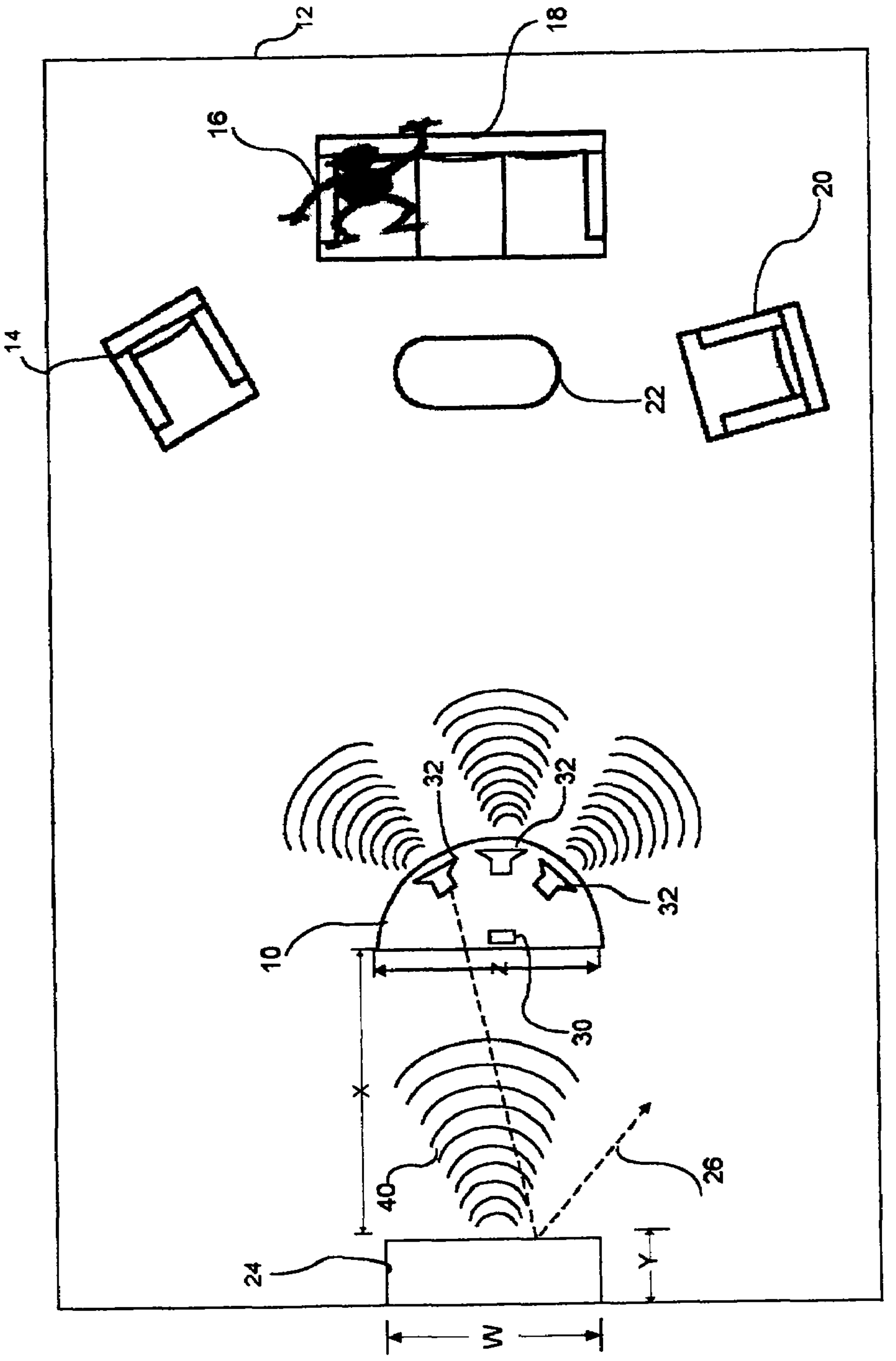
FIG. 1 is a schematic diagram illustrating the noise reduction system of the present invention applied to an example area having a noise source.

A schematic diagram illustrating the noise reduction system of the present invention applied to an example area having a noise source is shown in FIG. 1. The noise reduction system, generally referenced 10, is preferably placed very close to a noise source 24. The distance X is the distance between the noise source and the system 10. The smaller the distance X between the noise source and the system, the better the noise cancellation achieved. The system 10 comprises an input transducer 30 such as a microphone and one or more output actuators such as loudspeakers. In the example system shown in FIG. 1, three output actuator loudspeakers 32 are shown. The orientation of the output actuators is such that the sound waves generated by the output actuators cancel the noise source sound waves.

The noise source 24 is shown generating acoustic sound waves 40 that are sensed by the input transducer 30 in system 10. The width of the noise source is denoted by the value W and its length is denoted by the value Y. The system 10 is located from the noise source at a distance X. The width of the system is denoted by the value Z.

The noise source and the system are shown in a typical application such as a living room environment in a residence. The living room area 12 comprises typical furniture found in a living room, for example, two chairs 14, 20, a coffee table 22 and sofa 18. A person 16 is shown seated on the sofa and positioned within the effective quiet zone of the system. Although the noise source 24 and the system 10 are shown as separate entities, an alternative is to place both the system 10 and the noise source within a single enclosure (not shown). If the noise source is placed outside the enclosure, the enclosure is regarded as the noise source. The size of the noise source 24 influences the cancellation of the noise source acoustic waves. If the dimension Y of the noise source is large relative to the wavelength of the shortest interference noise signal, then a second noise reduction system should be installed on the other side of the noise source in order to achieve cancellation on that side.

The mechanical structure of the output actuator used in the system has an effect on the quality of the noise reduction achieved. This is especially true in the case when the width W of the noise source is bigger then the width Z of the system which is related to the length of the output actuators. Preferably, the system 10 is a symmetric structure built from many small output actuator elements wherein each output actuator is oriented in a different direction. The output actuator elements may be spread over the length of the housing enclosing the system in order to provide coverage up to 180 degrees. Note that only one input transducer 30 (e.g., microphone) is connected to the noise reduction system 10. Each of the output actuators drive the same phase of noise cancellation wave. The number of output actuators can vary in accordance with the particular application and may be reduced to one. Alternatively, the input transducer and the output actuator can be combined in a hybrid input/output element that is positioned against the noise source.

In a case of a hybrid transducer and the use of a plurality of output actuators, only the central actuator is used as a transducer. In the case of both separate input/output transducers and a hybrid transducer, the input transducer 30 must be oriented in a direction towards the noise source 24. The output transducers 32 must be oriented in a direction opposite the noise source. If a plurality of output actuators is utilized, then the centrally located transducer is oriented in a direction opposite the noise source. The output actuators other than the centrally oriented one must be positioned so as to achieve good noise cancellation, especially when a small number of output actuators is used. The proper position for the output actuators can be calibrated either manually or automatically at the time the system 10 is installed. Automatic calibration can be performed utilizing two motors (not shown), each oriented to handle a different axis of motion, attached to the output actuators. The proper calibration angle is determined by using the motors to adjust the position of the actuators to the angle that yields maximum detected power at the input transducer or sensor 30.

The total response time of the system, from the time the noise sound waves reach the input transducer to the time the noise cancellation signal is output by the output actuator, is preferably as short as possible. The effective length X is increased by an amount equivalent to the system delay time for the highest frequency component of the noise source wave.

In general, the system 10 detects the noise source using the input sensor 30, amplifies the noise with inverse polarity and outputs it through the output actuator 32. Since the output actuator and the input transducer are located vary close to each other, the contribution of the noise signal to the amplitude of the input signal is much lower than that of the output transducer.

In some configurations the noise cancellation signal generated by the output actuator may be reflected from the noise source as shown by the dashed line 26, thus increasing the overall level of noise in the system. To eliminate this type of reflected noise, a delayed cancellation signal is output by the system.

Figure 2:
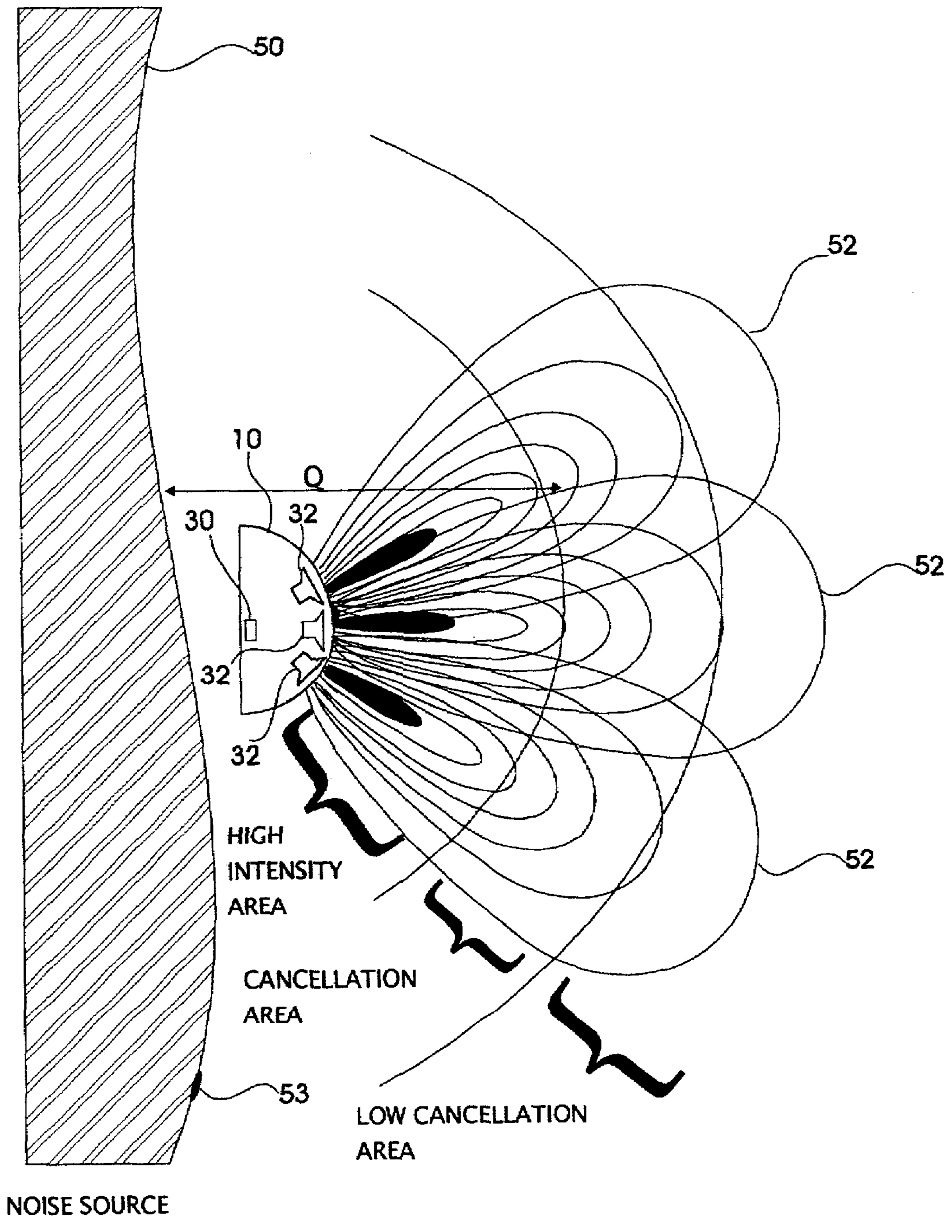
FIG. 2 is a schematic diagram of a single noise reduction system applied to reduce the effect of a noise source showing the acoustic beam patterns generated.

The acoustic noise cancellation method of the present invention is based on the behavior of the acoustic beam pattern in the air of the noise and the signal output by the system. A schematic diagram of a single noise reduction system applied to reduce the effect of a noise source showing the acoustic beam patterns generated is shown in FIG. 2. Good noise cancellation is achieved in an area far both from the noise source and the input transducer/output actuator while in areas close to the noise source there may be zones having higher levels of noise. Note that the system can effectively cancel noise at any arbitrary frequency regardless of whether the noise signal is periodic or not and without requiring any synchronization with the noise source.

The distance Q from the noise source represents an area of relative quiet. The length of Q is determined by the output power of the noise cancellation signal output by the system. Since the acoustic beam pattern is dependent on the characteristics of the output actuators and on the main frequency of the cancellation signal, it may be necessary to use different output actuators or to change the angle between them in order to achieve optimum noise cancellation for noise sources having different frequencies. For noise sources with complex surfaces, it is possible to achieve good noise cancellation when the distance from the noise source to the point of cancellation is larger then the noise source itself.

With reference to FIG. 2, a plurality of output actuators 32 is shown generating an anti-noise signal in response to a noise source 50. The sound waves 52 of the anti-noise combine with the original noise waves at a point far from the noise source thus creating a quiet zone. When a plurality of output actuators is used, each of the actuators creates its own anti-noise field oriented at a specific angle. The acoustic field of all of the output actuators acting together combine with the noise source acoustic field to create a high intensity area, a high cancellation area or quiet zone and a low cancellation area. The low cancellation area 52 is due to the effect of noise emitted from points such as 53 that are far from the system 10. Better noise cancellation is achieved if the noise source body generates homogenous noise, i.e., all of the points 53 generate noise having the same phase. The distance of the quiet zone from the noise source is dependent on the energy content of the anti-noise.

Figure 3:
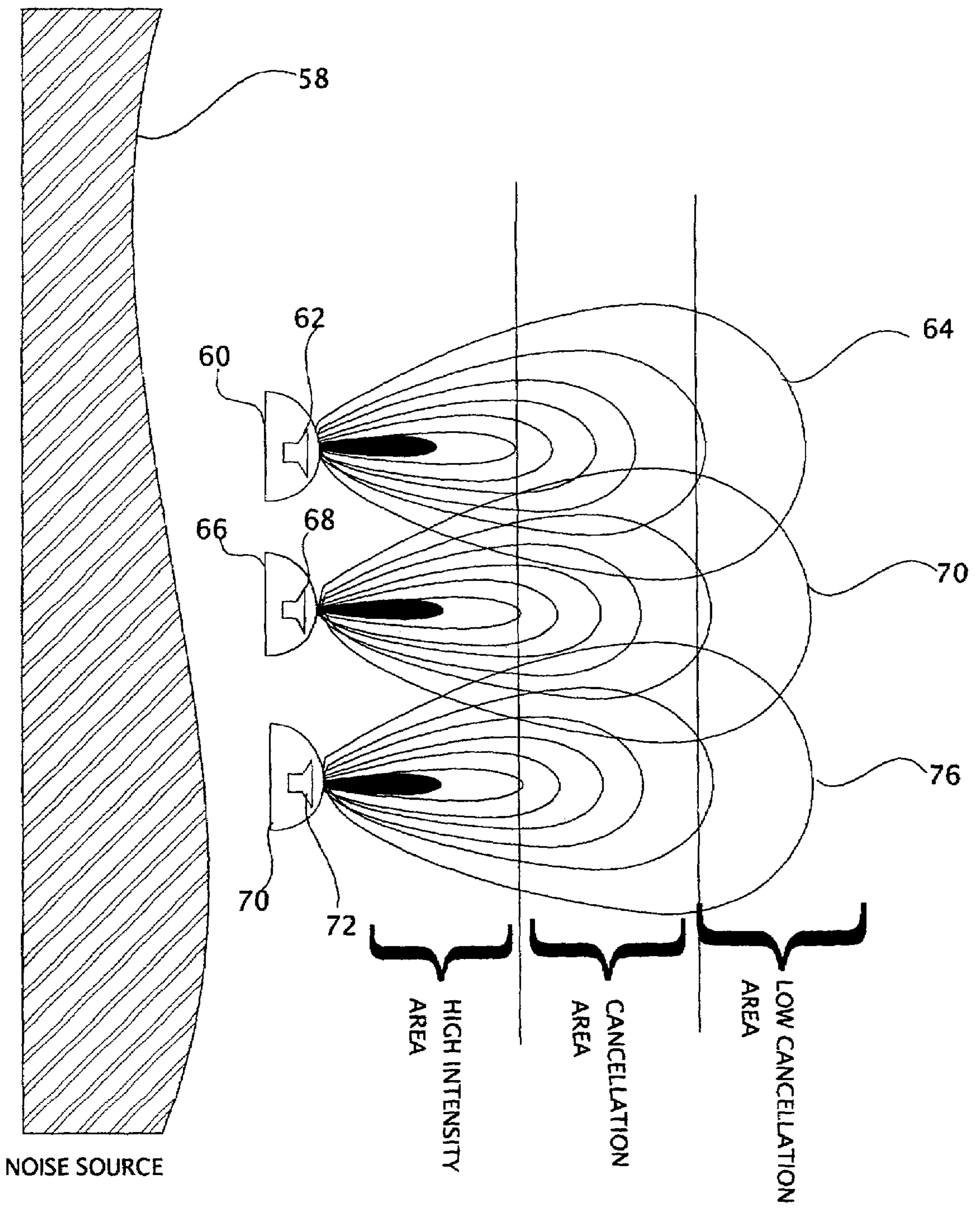
FIG. 3 is a schematic diagram of a plurality of noise reduction systems applied as an array of elements to reduce the effect of a noise source showing the acoustic beam patterns generated.

A schematic diagram of a plurality of noise reduction systems applied as an array of elements to reduce the effect of a noise source showing the acoustic beam patterns generated is shown in FIG. 3. This scheme is utilized when the surface of the noise source is large and complex or when it is difficult to place the noise reduction system close to the noise source. Noise cancellation is optimum when the noise generated by the noise source at a particular point on the body of the noise source has the same phase as the noise emitted from other points on the body of the noise that are oriented in the same direction.

Three noise reduction systems 60, 66, 70 are utilized in this example to reduce the effects of the noise source 58. The output actuator 62 of the system 60 functions to generate an anti-noise sound field 64. The output actuator 68 of the system 66 functions to generate an anti-noise sound field 70. Similarly, the output actuator 72 of system 70 functions to generate an anti-noise sound field 76. Thus, an array of independent output actuators 62, 68, 72 is used to create a quiet area at a distance from the array. The effectiveness of the virtual wall of quiet generated by the system is determined by numerous parameters. Such parameters include the distance between the individual noise reduction systems, the mechanical and electrical characteristics of the output actuators in relation to the main noise frequency, and the combined energy generated by the output actuators.

Figure 4:
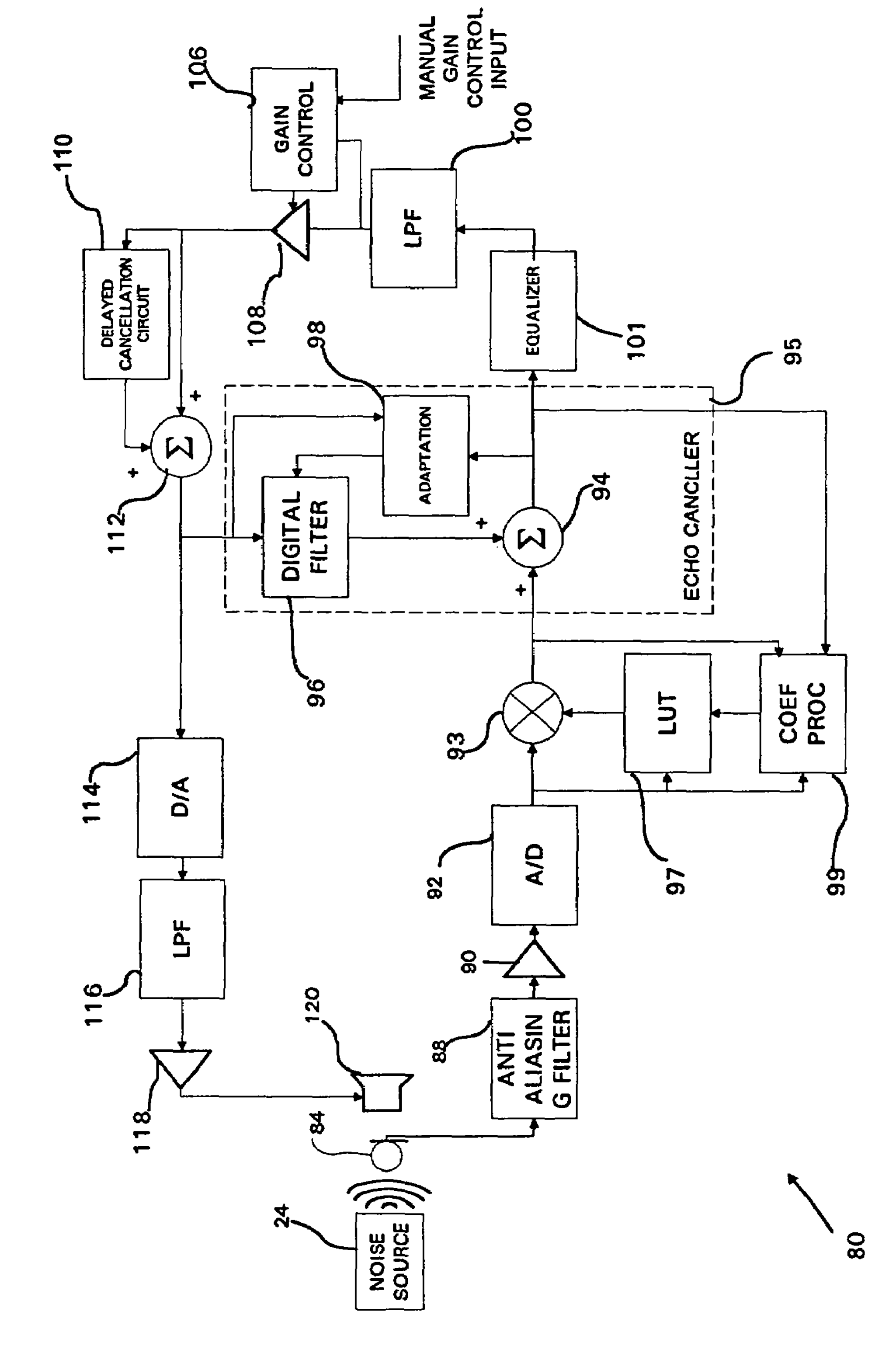
FIG. 4 is a block diagram of a first embodiment of the noise reduction system of the present invention utilizing echo cancellation.

A high level block diagram of a first embodiment of the noise reduction system of the present invention utilizing echo cancellation is shown in FIG. 4. The first embodiment, generally referenced 80, of the system comprises means for sensing the noise source, generating an anti-noise signal and outputting this anti-noise signal through one or more output actuators. In addition to sensing the noise source, the input transducer also senses the anti-noise signal output by the output actuator. As described previously, the amplitude of the anti-noise is larger than the amplitude of the noise signal itself. Echo cancellation is utilized to cancel the portion of the input signal associated with the signal output by the output actuator. If the input and output transducers are acoustically separate elements and there exists acoustic delayed feedback in the system, then using an echo cancellation system is preferable. If there is no acoustic delayed feedback from the output actuator to the input transducer, then a computing algorithm may be utilized to extract the noise signal from the total input signal.

The input portion of the system comprises an input transducer 84, anti aliasing filter 88, amplifier 90 and A/D converter 92. The input transducer may comprise a microphone, which is preferably directional and exhibits a very short delay. Use of a directional input transducer directed towards the noise source minimizes the sensitivity to acoustical inputs other then the noise source. It is also desirable for the microphone to filter the acoustic input to maximize the sensitivity for the frequency range in use.

Input transducers suitable for use with the present invention include, for example, electromagnetic based transducers, mechanical accelerators, electrical accelerators, piezoelectric and piezoceramic elements, vibration sensors, a capacitance microphone, a silicon microphone, and an optical microphone.

The analog signal output by the input transducer is then passed through an anti aliasing filter 88 to the analog amplifier 90. The anti aliasing filter 88 is a low pass filter (LPF) having a cutoff frequency of approximately 1 MHz and is constructed to exhibit minimum delay. The fixed gain analog amplifier 90 is adapted to reduce input transducer sensitivity to the minimum needed in order to eliminate the response of the system to sounds originating from sources other than the noise source. The signal output from the fixed gain analog amplifier 90 is then converted to digital via A/D converter 92. The A/D converter is sampled at a rate of approximately 1 M samples/sec and has a resolution of at least 12 bits with 16 bits being preferred.

The digital data output from the A/D converter is then adjusted to compensate for non linearities in the output transducer. Compensation for non linearities include multiplying the digital data by a coefficient stored in a look up table (LUT) 97 via the multiplier 93. The coefficients are calibrated dynamically during operation of the system. A coefficient processor 99 functions to calibrate the LUT coefficients based on the digital data output of the A/D converter and the output of the summer 94.

The output of the multiplier 93 is input to an echo canceler 95 which functions to remove the echo reflected back from the output actuator and picked up by the input transducer. The cancellation signal generate by the echo canceler 95 is added to the output of the multiplier 93 via summer 94. The output of the summer is input to the equalizer 101 that comprises a digital filter for correcting the frequency response gain and group delay of the analog elements in the system, including the output actuator and the input transducer. The equalizer causes the input signal having different frequencies to be generated at the output transducer after a fixed time delay. The output of the equalizer 94 is input to a low pass filter 100 which limits the maximum frequency within the system. LPF 100 comprises a digital finite impulse response (FIR) filter or infinite impulse response (IIR) filter having a low latency in the pass band. The use of the digital low pass filter 100 having a very short delay is optional but is useful to limit the band pass of the system to help avoid high frequency oscillations caused by the effect of feedback.

The output of the digital low pass filter 100 is input to a variable gain digital amplifier 108 whose gain is controlled by a gain control circuit 106. The variable gain amplifier functions to perform an inversion of the noise signal to generate an anti-noise signal which functions to cancel the effects of the noise. Thus, the gain control circuit 106 sets the gain of the amplifier to a negative gain value. In addition to generating the basic anti-noise signal, the amplifier 108 functions to prevent oscillations from occurring in the system. This is achieved by controlling the gain of the amplifier 108. The gain of the amplifier can be adjusted relatively slowly and does not have to be performed in real time.

A second input to the gain control circuit 106 is a manual gain control input that is provided by a user. A user can interact with the noise reduction system 10 by adjusting the gain of the amplifier 108. Using a suitable input device such as a remote control, a user positioned such as shown in FIG. 1, can control the location of the quiet zone to be any distance from the noise source by adjusting the gain of the amplifier. The gain adjustment capability of the noise reduction system is meant to achieve maximum cancellation at any arbitrary point within the cancellation zone. The gain may be preset or adjusted manually, such as by remote control. The gain control circuit 106 also comprises protection against the gain being increased too high so as to cause oscillations.

The level of gain required to create a suitable quiet zone of high noise sound cancellation is dependent on several factors, e.g., the particular noise source, acoustics and dimensions of the area, the position of the user, etc. For known fixed sources of noise, e.g., air conditioners, vacuum cleaners, etc., the gain adjustment of amplifier 108 can be performed once at the time of installation of the noise reduction system. The gain control method is described in more detail hereinbelow.

The output of the amplifier 108 is input to a summer 112 and a delayed cancellation circuit 110. The output of the delayed cancellation circuit 110 is added to the output of the amplifier 108 via summer 112. The function of the delayed cancellation circuit is to generate a cancellation signal in response to reflections of the output signal from the output actuator (FIG. 1 at 26) produced by the noise cancellation system itself. The reflection is effected by the acoustical environment, the distance of the system from the noise source 24 and the frequency of the noise. The delayed cancellation circuit is based on a delay circuit in combination with a negative gain multiplier. In the alternative, the circuit can be based on a digital filter having the same impulse response as the reflected signal but with the opposite, i.e., negative, polarity. The noise reduction system 10 effectively considers the acoustic waves reflected from the noise source as a second mirrored noise source located at a distance equal to the distance between the noise source and the noise reduction system. The only difference being that the path of the acoustic sound waves from the second noise source is in the opposite direction from the sounds waves emitted from the noise source itself.

The output of the delayed cancellation circuit is added to the output of the amplifier 108. Note that the signal generated to cancel the first reflection may itself be reflected off the noise source to effectively create a third mirror noise source and so on and so forth. This third noise source can subsequently be canceled using the same method of the delayed cancellation circuit 110 but with different parameters (not shown).

Figure 5:
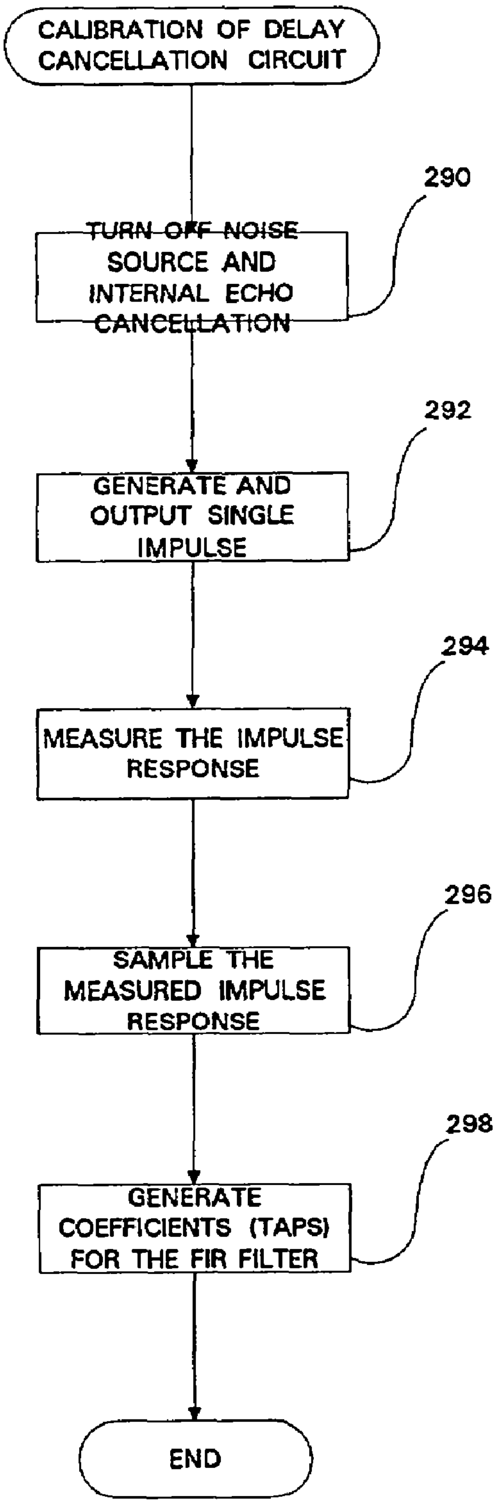
FIG. 5 is a flow diagram illustrating the calibration method of the delay cancellation circuit.

Note that the delayed cancellation circuit is optional but using it, however, can aid in canceling acoustic sound waves fed back from the noise source body. Calibration of the gain and the delay of the impulse response of the delayed cancellation circuit 110 is performed once during installation of the noise reduction system 10. A high level flow diagram illustrating the calibration method of the delay cancellation circuit is shown in FIG. 5. The calibration procedure comprises first turning off the noise source and the echo canceler within the system (step 290). Then, a single impulse is generated and output through the output actuator (step 292). The impulse is generated towards the noise source while the noise source itself is off. The impulse response is then measured, i.e., the input fed back from the noise source is measured (step 294). The noise reduction system 10 regards this source of noise as a second noise source having known characteristics.

The measured impulse response is then sampled (step 296) and FIR filter coefficients are generated based on the sampled impulse response (step 298). The gain of the delayed cancellation circuit 110 is determined using the following equation.

$$GAIN_{DCC} = -GAIN_{AMP} \cdot \left(\frac{INPUT}{OUTPUT}\right)$$

Wherein $GAIN_{DCC}$ is the gain of the delay cancellation circuit, $GAIN_{AMP}$ is the gain of the variable gain amplifier 108, INPUT is the maximum amplitude of the response measured at the output of the A/D converter 92 before the data is corrected for non linearities and OUTPUT is the output impulse transmitted value of the variable gain amplifier 108. Thus, the gain of the delayed cancellation circuit (DCC) is based on the negative or inverted gain of the amplifier 108.

Note that the initial portion of the measured impulse response is due to the input transducer picking up the output of the output actuator without echoes, reflections or feedback. The actual response to the impulse function does not begin until a certain time period after the impulse is generated. This time period is proportional to the system time delay period and can be calculated since the start of the impulse function and the measured response are known. The portion of the impulse response prior to the system delay period is discarded and not used to generate the coefficients for the digital FIR filter that can be utilized in the delayed cancellation circuit. The system delay time is defined as the time from impulse generation until the time that the amplitude of the first response at the output of the A/D converter 92 is equal to 0.2 of the maximum amplitude response. For example, if it is assumed that the system delay time is 100 μs, then the first 100 μs of the measured impulse response is discarded. The portion of the response 100 μs and beyond is sampled and used to generate the filter coefficients. If the system includes cancellation circuitry for the third mirrored noise source, then the calibration is performed in steps. In the first step, the second mirrored source cancellation coefficient calibration is performed as described above. With this cancellation activated, calibration of the second step is performed by repeating the procedure described in FIG. 5. The new coefficients are derived from the second feedback filter (not shown).

The output of the digital summer 112 is input to the D/A converter 114 and to the echo canceler 95 portion of the system. The echo canceler 95 comprises a digital filter 96, an adaptation circuit 98 and a summer 94. The echo canceler 95 functions to remove reflections of sound and prevent oscillations caused by the output of the output actuator feeding back to the input transducer. The filter 96 is a digital FIR filter having a sufficient number of taps, i.e., delay, to cover the round trip delay through the system as well as feed back echoes from the acoustical environment.

In order to reduce the computation burden of the FIR, interpolation and decimation methods, well known in the digital filter arts, are used (not shown) at the FIR output and input, respectively. The coefficients of the FIR filter correspond to the coefficients of the impulse response of the portion of the system from the output of the summer 112 to the input of the summer 94 and are measured and setup at the time the system is started up. The measurements is performed by using the maximum length sequence technique (MLS), a technique well known in the art. The MLS technique is implemented by generating the MLS pseudo random sequence at the output of the summer 112, measuring at the input to summer 94, and then low pass filtering the cross correlation of the two signals. The results of the MLS measurement are the filter 96 coefficients.

Real time adaptation of the digital filter coefficients by the adaptation circuit 98 is performed using any suitable FIR adaptation algorithm well known in the art, such as the least mean squares technique. The adaptation is based in the error signal output by the summer 94.

Since the input noise signal from the noise source 24, e.g., motor or airflow noise, is a highly correlated signal, the regular FIR adaptation is applicable only outside of the auto correlation area. For example, in a typical air conditioning system, the auto correlation signal is 300 microseconds. Assuming a system delay of 100 microseconds, there are 300 minus 100 or 200 microseconds that may not be calibrated using the least mean square technique.

If the length of the FIR is adapted to be 5 milliseconds, then only the last 4.8 milliseconds may be adapted in real time using the least mean square (LMS) technique using a special variance explained bellow. Note that the LMS technique is well known in the art. The coefficients within the first 200 microseconds change relatively slowly with time and are effected mostly by temperature and humidity. Calibration of the coefficients within the first 200 microseconds is performed slowly in real time using the MLS technique described above with the exception that no generation of signal occurs. Instead, the noise data is used to perform cross correlation. Averaging a large number of test results yields the coefficients for the first 200 microseconds of the FIR filter 96. Note that when using the local closed loop control system to control the linearity of the output actuator as described in the linearity table, there is no need to adapt the first 200 microseconds in real time since the system response during that time is constant.

The noise is cyclic, i.e., repetitive, and to enable acceptable adaptation, only one noise cycle is enabled within the length of the FIR filter. The full length of the FIR filer is divided into a plurality of short FIR filters. For example, if the noise cycle is 600 Hz, then the maximum allowed FIR length is 1/600=1.6 milliseconds. To cover the full 4.8 milliseconds, three short FIR filters are used wherein each filter spans 1.6 milliseconds. Each FIR filter comprises it's own separate adaptation circuit.

Figure 6:
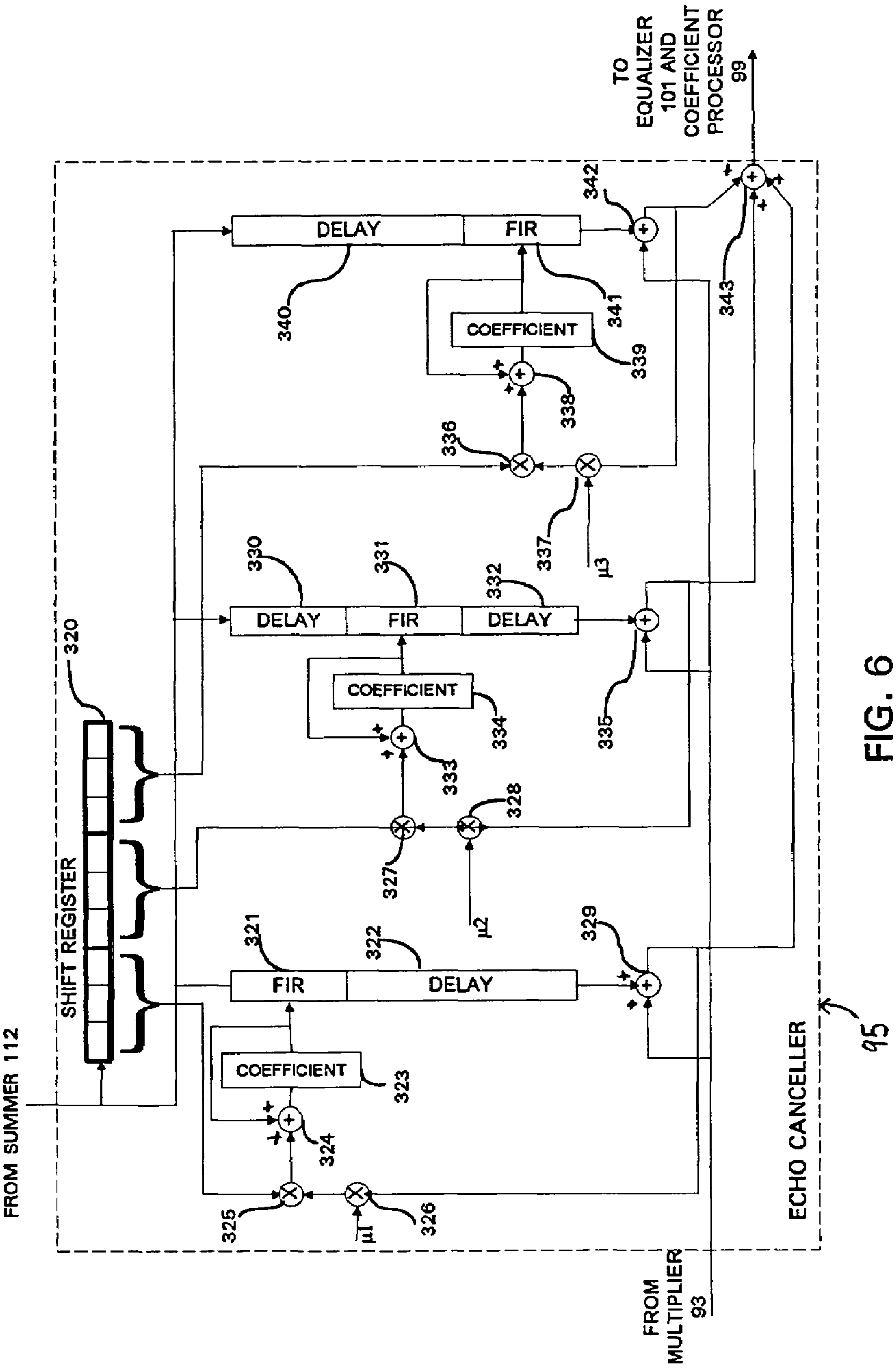
FIG. 6 is a block diagram illustrating the echo cancellation portion in more detail.

The block diagram shown in FIG. 6 illustrates the difference between a conventional LMS adaptation and the LMS adaptation of the present invention. Three FIR filter units are used with three taps in each FIR filter. The data from the summer 112 is input to the shift register 320 that functions as a serial to parallel converter. The first three registers 1, 2, and 3 of the shift register 320 are utilized by the first FIR 321 in accordance with the following. The input noise that comes from multiplier 93 is multiplied by the constant μ1 via multiplier 326. The resulting product is multiplied with the contents of the first three registers of shift register 320 via multiplier 325. The resultant product is subsequently added to the current coefficient 323 via adder 324.

It is important to note that the size of the coefficient 323 and the size of the FIR filter is ⅓ of the total length of the FIR filter. The remainder of the length is used as a shift register delay 322. The FIR portion 321 and the shift register delay portion 322 combine to from the complete FIR length. The summer 329 sums the output of the FIR with the input from multiplier 93 to generate first part of the result. The output of the summer is input to the summer 343.

The second set of three registers 4, 5 and 6 are delayed in sync with delay 330 which generates a delay equal to the length of FIR 321. The output of the delay 330 is input to FIR 331. The coefficient 334 adaptation is performed using multipliers 328 and 327 and adder 333 in a manner similar to that of the adaptation of coefficient 323 but utilizing constant μ2 and registers 4, 5 and 6. The output of the FIR 331 is input to delay 332 to complete the length of the FIR. The output of delay 332 is summed with the input from multiplier 93 via adder 335 to yield the second part of the result which is input to summer 343.

The third portion of the output of summer 343 is generated utilizing bits 7, 8 and 9 of shift register 320 after passing the data through delay 340 and FIR 341. The coefficient 339 adaptation is calculated using μ3, the input signal from multiplier 93, the output of multipliers 337, 336 and the output of adder 338. Note that the length of delay 340 is equal to the length of FIR 321 plus the length of FIR 331. Thus, FIR 341 functions to complete the total length of the FIR filter.

The dynamically changing values μ1, μ2 and μ3 function to determine how fast the adaptation algorithm performs. For example, if the adaptation algorithm runs too fast, the LMS will not yield correct results, i.e., it may not converge. A typical value for μ1, μ2 and μ3 is in the range of 0.1 to 0.2 which was derived from experimentation.

The output of the summer 94 is a digital signal wherein the feedback, i.e., echo, caused by the generated output signal has been removed. The digital filter 96 functions to generate a signal that is substantially the opposite of the portion of the input signal that is fed back from the output signal.

The response of the adaptive digital filter 96 is the same response of that of the system from the output actuator to the input transducer including the environmental acoustic effects. The digital filter 96 functions to generate the signal output by the output transducer but with opposite polarity, i.e., negative polarity and the correct phase shift and amplitude. The summer 94 adds the output of the digital filter 96 with the output of the multiplier 93, which is the digital input corrected for the non linearities of the input transducer, to eliminate the echo from the input signal. The addition operation performed by summer 94 may be performed digitally as described above or can be performed in analog. The summing can be performed in analog by utilizing a D/A converter to convert the output of the digital filter 96 to analog and summing the result with the analog signal from the input transducer. In the case of the analog echo cancellation summation, it is not economical to use an analog multiplier for the linearity table and thus, the assumption is that the actuator is linear. In either case, the output of the echo canceler is input to the digital low pass filter 100 as described hereinabove.

It is important to note that the time response of the digital filter 96 must be long enough to cancel all of the acoustical sound fed back to the input transducer from the output actuator. The adaptive echo canceler 95 adjusts the filter taps in response to changes in the acoustical environment, e.g., temperature, furniture placement, etc.

The output of the summer 112 is input to the D/A converter 114 which functions to convert the digital signal into analog. The output of the D/A converter 114 is input to an analog low pass filter 116. The cutoff frequency of the low pass filter 116 is approximately 1 MHz. The output of the low pass filter 116 is input to the power amplifier 118. The power amplifier boosts the level of the output sufficiently to drive the output actuator 120. The output actuator can be any suitable device that transforms the output signal to sound waves. The output actuator can comprise a loudspeaker having a relatively short delay. The output actuator 120 may comprise a single output actuator or a plurality of output actuators connected in parallel.

In addition, the system of FIG. 4 also comprises a controller (not shown) which functions to administer and control the configuration, operation, settings and all timing of the noise reduction system 10.

It is noted that the sound emitted from the output actuator is detected by the input transducer at a much higher amplitude than the noise itself. The noise reduction system 10 functions to discern the much smaller noise signal from the much larger echo signal. However, the input transducer exhibits a non linear response to the amplitude of the sound waves incident on it. It turns out that the input/output response of the input transducer, such as a microphone comprising a membrane, is dependent on the total amount of power hitting the microphone. Thus, for the same amplitude noise signal, the linearity of the microphone is different for an input with low total power input as compared to an input with high total power. Thus, the high amplitude signal output from the output actuator effects a different relative output signal from the input transducer due to the noise. This is especially true when using a hybrid to perform both the input and the output transducer functions of the system. Non linearity at the output actuator is manifested when the output peak power to the transducer is large. When using separate input/output devices, the non linearity in the output device is much more critical when the mechanical amplitude is large. The operation of the system is based on the correct discrimination of the noise source from the much larger echo signal. Thus, a correction of the echo signal amplitude as it appears in the input is required in order to achieve good cancellation of the echo signal. The linearity LUT performs this correction operation by multiplying each input value with the correction coefficient. The linearity table may be generated a priori and calibrated at the time of installation or adjusted dynamically on the fly. The linearity table and the dynamic adjustment of its contents are described in more detail hereinbelow.

As an alternative to the linearity table, a local closed loop control system can be used to compensate for the linearity of the actuator (not shown). Such a technique is described, for example, in the proceedings of Active 97 in the article by Yoon-Sun Kim and Youngjin Park entitled "Non Linearity Compensation for Harmonic Distortion of Direct Radiation Loudspeaker."

Figure 7:
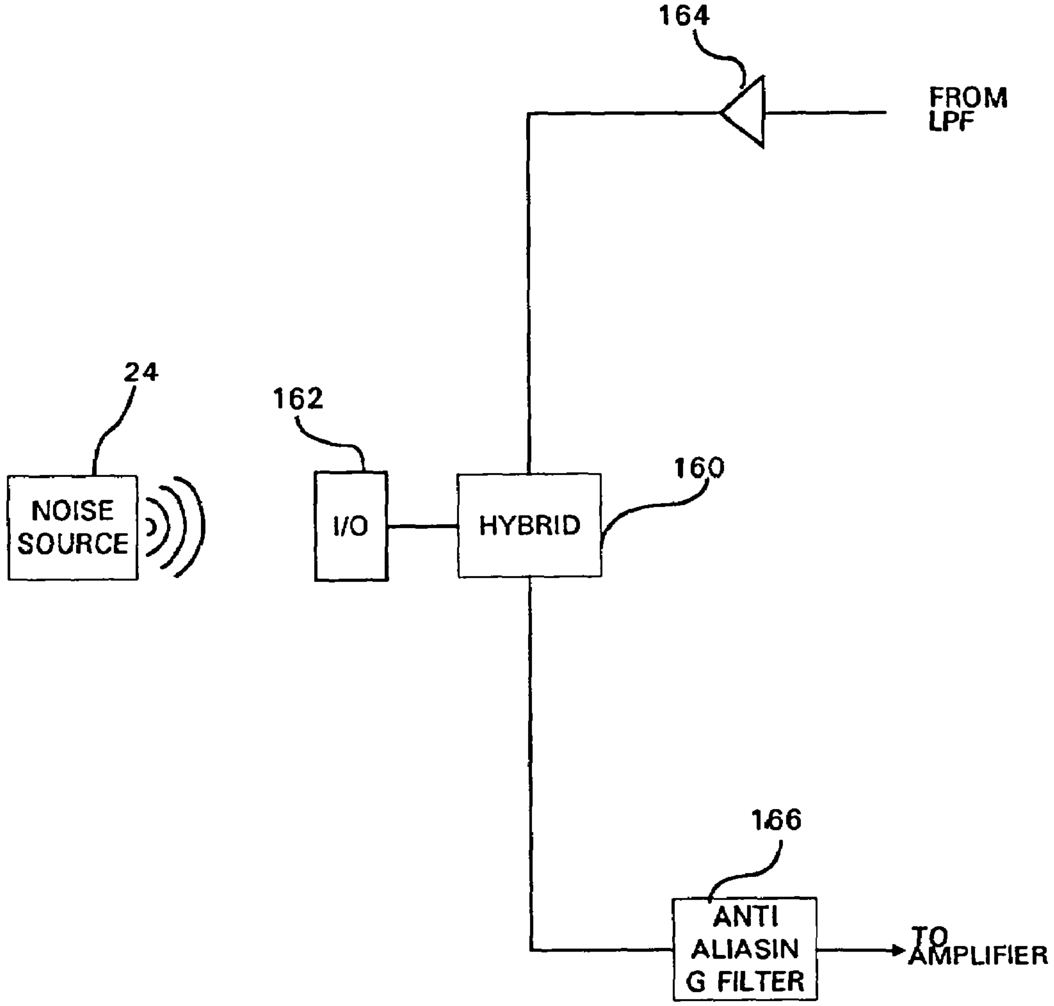
FIG. 7 is a block diagram illustrating the input transducer and output actuator implemented as a hybrid combination in a single element.

A high level block diagram illustrating the input transducer and output actuator implemented as a hybrid combination in a single element is shown in FIG. 7. As an alternative to a separate input transducer and output actuator, a hybrid input/output (I/O) element or transducer 162 can be utilized that performs the functions of both elements. In this case, a hybrid circuit 160 is needed to interface the I/O element 162 to the power amplifier 164 and the anti aliasing filter 166. The hybrid 160 functions to transfer power from the power amplifier 164 with minimum losses to the I/O transducer element 162 and with maximum reduction to the anti aliasing filter 166.

Figure 8:
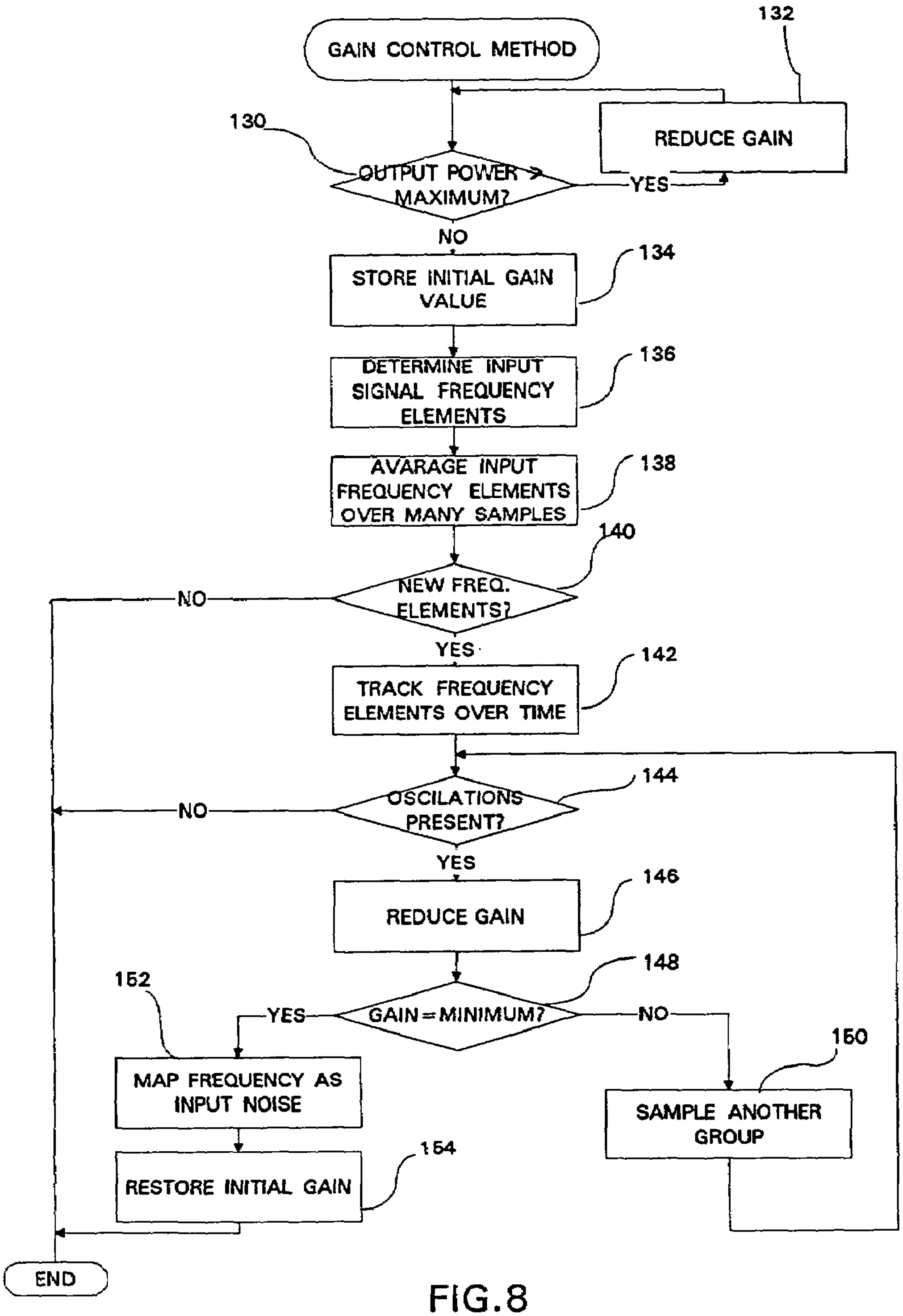
FIG. 8 is a flow diagram illustrating the gain control method utilized in the first and second embodiments.

The gain control method implemented in the gain control circuit 106 (FIG. 4) of the variable gain amplifier 108 will now be described in more detail. A high level flow diagram illustrating the gain control method utilized in both the first and second embodiments is shown in FIG. 8. This method operates in a loop to continuously search for oscillations in the system. In general, an FFT performed in the gain control circuit is used to map the mean amplitude of the frequency content in the detected input. When a new frequency is detected or when the total input power to the system increases, an immediate reduction of the gain of the amplifier 108 is performed.

The first step is to check the total power of the output signal to see if it is over a predetermined maximum (step 130). If the power is over the permitted maximum then the gain is reduced until the total output power is below the maximum (step 132). Once the gain is within the permitted range, the current gain setting is stored as the initial gain value (step 134). A Fast Fourrier Transform (FFT) is then performed on the signal input to the amplifier (step 136). The FFT yields a map of the frequency content of the input signal. A plurality of samples of the input are taken and FFT analysis performed on each sample. Corresponding frequency elements are averaged over many samples (step 138).

It is then checked for the significant presence of signal content at new frequencies (step 140). If signal content is found at new frequencies, these frequencies elements are tracked over time (step 142) to determine whether they are oscillations (step 144). A new frequency that is persistent in time is considered a suspect oscillation. If there is a suspected oscillation, then the gain is reduced by a step amount (step 146). If the gain is reduced to a predetermined minimum (step 148) the frequencies that were suspect as oscillations are mapped as input noise, i.e., a frequency generated by the environment with a particular amplitude and frequency range and not as oscillations (step 152). This is because, at such low values of gain, it would be highly improbable that the suspect frequencies were caused by oscillations. Signals within the frequency range are treated as environmental noise. After the environmental frequencies are mapped, the gain is restored to the gain that was initially saved during step 134.

If there are no new frequency elements in step 140 or oscillations suspected in step 144, the method ends. If the gain in step 148 is not a minimum, than another group of samples is input (step 150). After sampling another group of input signals, it is then checked whether oscillations are still present after the gain has been reduced. The method keeps looping by checking for oscillations, reducing the gain if oscillations are found and generating additional input sample until either no oscillations are found or the gain reaches a minimum.

As described previously, the linearity LUT 97 is used to correct the non linear behavior of the input/output transducers. Since typical input transducers are constructed from moving mechanical parts, the output response for the same input noise level is different for different levels of total input power incident on the input transducer. However the output actuator suffers from non linearities when the motion of the moving mechanical parts increase as a result of increasing output power. The difference in output response of the output actuator and input transducer is corrected utilizing the linearity LUT 97. The linearity LUT stored different coefficients for each amplitude input value range. The linearity LUT is divided into regions with each region having its own coefficient value. For example, assuming a 12 bit data word, the linearity LUT may be divided into 256 regions, thus only utilizing 8 bits of the input data. Upon startup of the noise reduction system 10, all of the coefficients in the linearity LUT have the same value.

The present invention includes a first and a second method of calibrating the linearity LUT. Both methods are performed in real time during the operation of the noise reduction system. Both calibration methods utilize a linearity look up table (LUT) that holds coefficients used to adjust the input data output by the A/D converter. The adaptation or calibration of the coefficients of the linearity LUT serves to compensate for slow changes to the linearity of the system caused by temperature, etc. The linearity LUT also functions to compensate for the mechanical non linearities of both the input transducer and the output actuator(s). Although not necessary to perform the invention, the input amplitude is divided into a plurality of regions wherein each region has a coefficient associated with it.

The first calibration method utilizes the input noise signal itself to calibrate the coefficients. In the second method, a small amplitude calibration signal is injected into the system during operation and the results used to generate new coefficient. Each calibration method will now be described in more detail below. The high level flow diagrams describing the linearity table calibration methods refer to the calibration of one coefficient. The methods described are repeated in order to calibrate all the coefficients.

Figure 9:
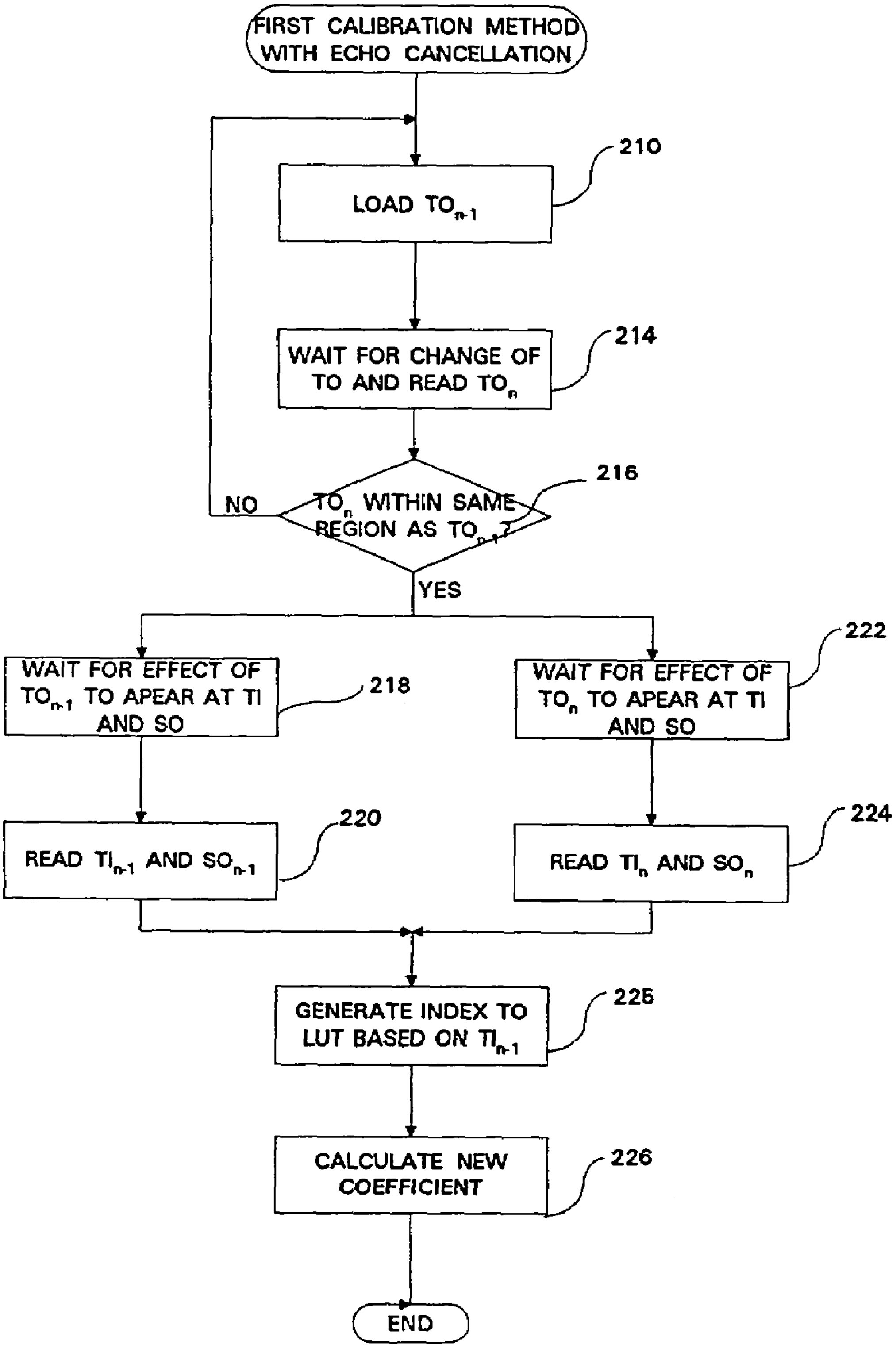
FIG. 9 is a flow diagram illustrating the first calibration method associated with the first embodiment.

A high level flow diagram illustrating the first calibration method associated with the first embodiment is shown in FIG. 9. The first method of calibration utilizes the fact that the noise is physical and continuous. The controller in the system tracks the relationship between values termed Table Input (TI), Table Output (TO) and Summer Output (SO) during operation of the system. The TI values are measured at the output of the A/D converter 92 (FIG. 4), the TO values are measured at the output of the multiplier 93 and the SO values are measured at the output of the summer 94. The coefficient processor 99 functions to calculate new LUT coefficients based on the TI, TO and SO values.

The calibration of the LUT coefficients during operation of the system attempts to ignore the effects of the noise source. Note that the input noise source itself changes between two adjacent samples. Note also that the output of the summer SO represents the noise source since the echo canceler 95 effectively removes the echo signal from the input signal.

The following calibration method is based on the system time delay which is defined as the time from TO to the D/A 114 plus the time from the D/A 114 to the A/D 92. Note that factored in this time is the acoustic medium, the analog transducers the circuit and the time from the A/D 92 to TO. The time attributed to the acoustic medium and the analog transducers and circuit is substantially equivalent to the time during which most of the energy of the impulse generated at D/A 114 is measured at the A/D converter 92. The measurement of the impulse is performed using the impulse response measurement technique described previously in connection with the calibration of FIR filter 96.

The calibration method initially measures two TO values, i.e., a value at time 'n−1' and another at time 'n'. Subsequently, after a system time delay, the controller then measures the two TI and SO values that are the effect of the previously measured TO values, assuming the system time delay is known. In other words, each TI and SO value is measured after the corresponding TO values has had a chance to propagate through the system, i.e., output by the output actuator, sensed at the input transducer, etc. Note that the SO value is the TI value after compensation for non linearities and after the echo fed back from the output actuator to the input transducer is removed to yield a value that reflects the noise level only.

With reference to FIG. 9, the first step in the calibration method is to read a Table Output (TO) value at the output of the multiplier 93 (FIG. 4), termed $TO_{n-1}$ (step 210). After reading the $TO_{n-1}$ value, the system waits for the output of the multiplier to change before reading the next value which is termed $TO_n$ (step 214). During operation of the system, it is not unusual if the input data does not vary much from sample to sample. This is due to the fact that the sampling rate of the system is orders of magnitude higher than the frequencies making up the noise signal. In step 214, the system waits more then one sample time, and the sample is taken when the difference between the level of $TO_{n-1}$ and $TO_n$ reaches some minimum which is predetermined. This minimum determines the coefficient calibration accuracy. It is then determined whether $TO_n$ is within the same region of the LUT as $TO_{n-1}$ (step 216). This is checked in order to prevent two TO values being associated with different regions of the LUT. The calibration method calculates new coefficients for a single region of the LUT at a time. The calculations, thus, cannot span borders between regions.

Next, the system waits for the effect of the $TO_{n-1}$ value (step 218) and $TO_n$ value (step 222) to appear at the output of the A/D converter and the output of the summer. As described previously, the data output by the A/D converter is termed Table Input (TI) data and the data output by the summer is termed Summer Output (SO). Once the effect of the $TO_{n-1}$ data appears at the output of the A/D converter and the summer, the $TI_{n-1}$ and $SO_{n-1}$ values are read (step 220). Similarly, once the effect of the $TO_n$ data appears at the output of the A/D converter and the summer, the $TI_n$ and the $SO_n$ values are read $N_n$ (step 224). The steps of first waiting and then reading the TI and SO values described herein can be implemented either sequentially or in parallel.

The index to the LUT which determines which coefficient is presently under calculation is then generated using the $TI_{n-1}$ value read during step 220 (step 225). This index is used for the calibration process only and does not effect the main real time data path of the system. In the example noise reduction system shown in FIG. 4, the LUT has less entries in it than the number of possible input values, e.g., 256 regions for 12 bits of input data, in order to reduce the size of the lookup table required. Alternatively, the LUT can be constructed to hold a coefficient value for each and every possible input data.

Once the TI and SO data have been read, the new coefficients are calculated using the following equation (step 226).

$$C_{new} = C_{old} + K\left\{\left[\frac{TO_n - TO_{n-1}}{(TI_n - SO_n) - (TI_{n-1} - SO_{n-1})}\right] - C_{old}\right\}$$

The new coefficient $C_{new}$ is a function of the old coefficient $C_{old}$. The values TO, TI and SO are used to generate an intermediate new coefficient from which $C_{old}$ is subtracted. A portion of the delta is added to $C_{old}$ to perform the calibration. The constant K varies between 0 and 1 and is used to determine the speed with which the coefficients are permitted to change. Values of K closer to 0 cause the coefficients to change more slowly whereas values of K closer to 1 cause the coefficients to change more quickly.

Figure 10:
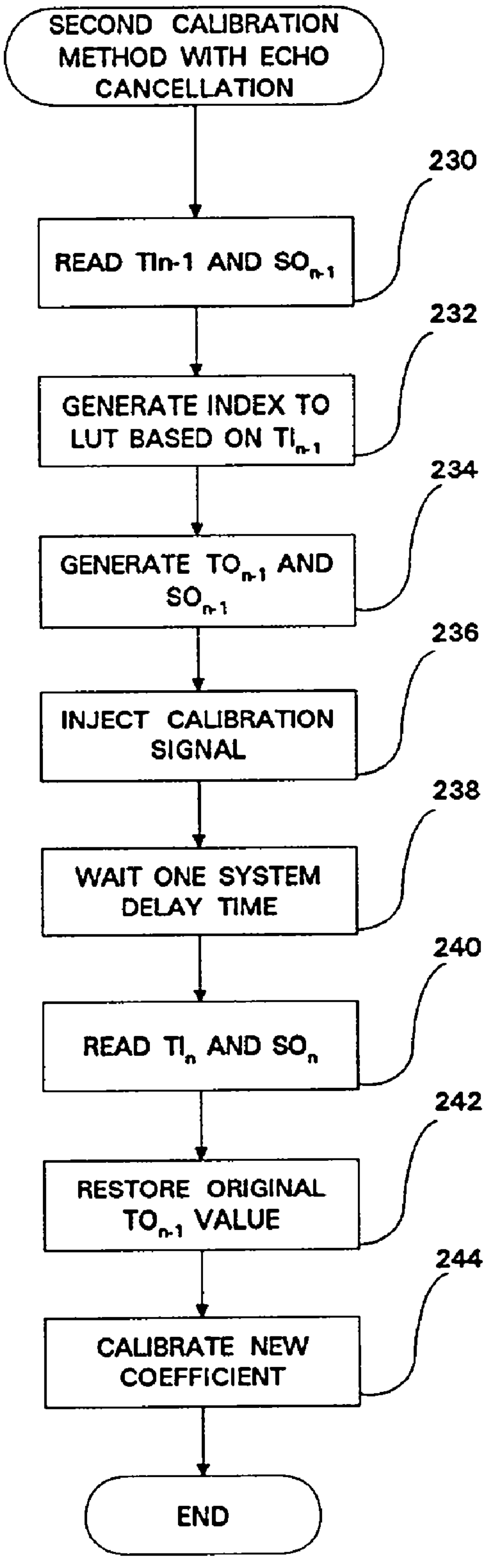
FIG. 10 is a flow diagram illustrating the second calibration method associated with the first embodiment.

The second calibration method associated with the first noise reduction embodiment of FIG. 4 will now be described in more detail. A high level flow diagram illustrating the second calibration method associated with the first embodiment is shown in FIG. 10. This second method of calibration is similar to that of the first method described in connection with FIG. 9, with the difference being that rather than wait for the actual noise source to cause a change to the TO value, an artificial noise signal is injected into the data path to simulate a known change in the noise signal level. The second method of coefficient calibration models the noise as a pseudo DC level noise source during calibration. This is a reasonable assumption since the calibration period of approximately 10 μs is very short relative to the noise frequency. This pseudo DC level of the noise is used to point to a particular region in the linearity LUT.

With reference to FIGS. 4 and 10, the first step is to measure the Table Input (TI) value denoted $TI_{n-1}$ at the output of the A/D converter 92 (step 230). The index to the linearity LUT is then generated based on the $TI_{n-1}$ value just measured (step 232). The index determines which of the coefficients of the linearity LUT is to be calibrated during this particular invocation of the method. The next step is to read the Table Output (TO) value, denoted $TO_{n-1}$, at the output of the multiplier 93 and the Summer Output (SO) value, denoted $SO_{n-1}$, at the output of the summer 94 (step 234). The TO value is generated by multiplying the output of the A/D converter with the output of the LUT. The result of the multiplication is added to the output of the digital filter. Note that the TO and SO values are read immediately after the TI value is read without waiting a system time delay as in the first method of FIG. 9.

A calibration signal is then injected at the output of the multiplier (step 236). The output of the multiplier which is denoted as the TO value is replaced with the calibration signal for a finite time period. The calibration signal, termed $TO_n$, comprises the original output of the multiplier $TO_{n-1}$ increased by a known delta amount. The system then waits one system delay time for the injected calibration signal to appear at the output of the A/D converter (step 238). After waiting one system time delay, the data at the output of the A/D converter is read and termed $TI_n$. In addition, the output of the summer 94, termed $SO_n$, is also read (step 240).

After reading the $TI_n$, value, the original output of the multiplier $TO_{n-1}$ before the calibration signal was injected is restored (step 242). Then, based on the values TI, TO and SO, the new coefficient can be calculated utilizing the following equation (step 244).

$$C_{new} = C_{old} + K\left\{\left[\frac{TO_n - TO_{n-1}}{(TI_n - SO_n) - (TI_{n-1} - SO_{n-1})}\right] - C_{old}\right\}$$

The new coefficient $C_{new}$ is a function of the old coefficient $C_{old}$. The values TO, TI and SO are used to generate an intermediate new coefficient from which $C_{old}$ is subtracted. A portion of the delta is added to $C_{old}$ to perform the calibration. The constant K varies between 0 and 1 and is used to determine the speed with which the coefficients are permitted to change. Values of K closer to 0 cause the coefficients to change more slowly whereas values of K closer to 1 cause the coefficients to change more quickly. Further, if it is assumed that within the relatively short calibration time, the noise source changes very little, i.e. $SO_n$ is equal to $SO_{n-1}$ in the equation above, these terms may be removed from the equation.

Figure 11:
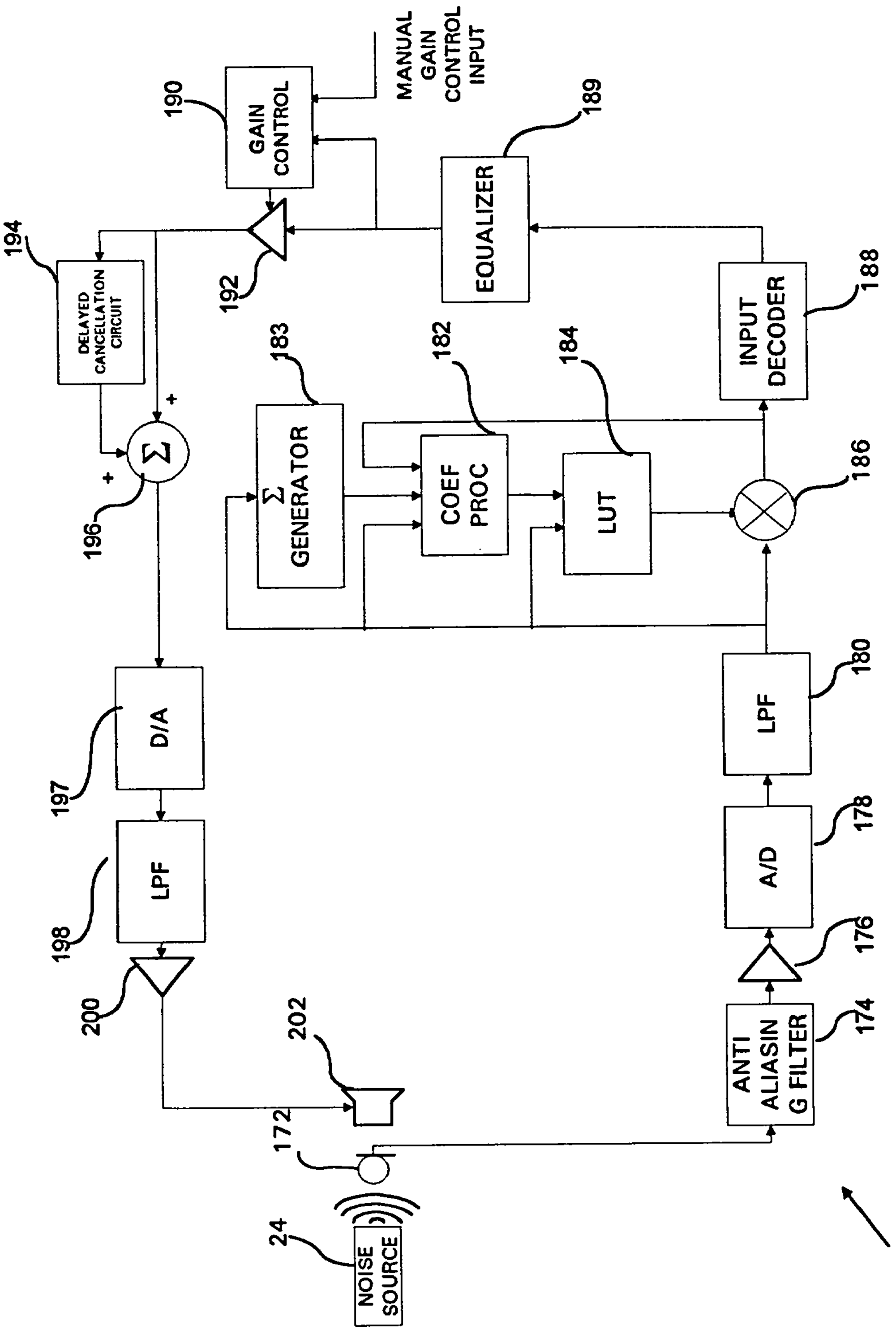
FIG. 11 is a block diagram of a second embodiment of the noise reduction system of the present invention utilizing a computational method to reduce echoes and oscillations.

The second embodiment of the noise reduction system of the present invention will now be described in more detail. A high level block diagram of a second embodiment of the noise reduction system of the present invention utilizing a computational method to reduce echoes and oscillations is shown in FIG. 11. The noise reduction system of FIG. 11, generally referenced 170, is constructed similarly to the noise reduction system 80 of FIG. 4. The difference being the system 170 does not include the echo canceler circuit 95. The system 170 comprises an input transducer 172 such as a microphone, anti aliasing filter 174, fixed gain amplifier 176, A/D converter 178 and digital low pass filter 180.

The output of the low pass filter is corrected for non linearities of the transducers via a non linearity correction circuit comprising multiplier 186, sigma generator 183, coefficient processor 182 and linearity look up table (LUT) 184.

The output of the multiplier is input to an input decoder 188 which functions to remove feedback picked up by the input transducer that was output by the output actuator. The output of the input decoder 188 is input to an equalizer 189 which comprises a digital filter that corrects the frequency response gain and group delay of the system analog elements including the output actuator and the input transducer. The result is that the frequency response of the combination of the input transducer and output actuator is flattened. The equalizer 189 causes the input signal, which lies within a particular frequency range, to be generated at the output transducer after a fixed delay.

The output of the input decoder is amplified via a variable gain amplifier 192 whose gain is set by a gain control circuit 190. The output of the variable gain amplifier is input to the delayed cancellation circuit 194 whose output is added to the amplified signal via summer 196. The output of the summer is input to a D/A converter 197. The output of the D/A converter is input to a low pass filter (LPF) 198. The output of the LPF is input to a power amplifier 200 whose output drives the output actuator 202 which may comprise a low delay loudspeaker.

Like components of the noise reduction system of FIG. 11 function similarly to the corresponding components of the noise reduction system of FIG. 4 and are thus described in more detail hereinabove. Note also that a hybrid I/O device can be used with the system 170 in place of a separate input transducer and output actuators.

The system shown in FIG. 11 is based on the system time delay which is defined as the time from the output of the summer 186 through the input decoder 186, amplifier 192, summer 196, D/A 197, low pass filter 198, amplifier 200, output actuator 202, acoustic medium, input transducer 172, filter 174, amplifier 176 and low pass filter 180. The time duration through the acoustic medium and the analog transducers and circuit comprises the time during which most of the energy of the impulse generated at the D/A converter 197 is measured at the A/D 178. The measurement (not shown) of the impulse is performed once during the start up phase of the system and considered as a constant during the system operation.

The goal of the noise reduction system of FIG. 11, as with the system of FIG. 4 also, is to detect the relatively low noise signal from the larger signal picked up from the output of the loudspeakers. The performance of the system of FIG. 11 is slightly less than the performance of the system of FIG. 4 due to the fact that the echo canceler 95 functions to cancel acoustic echoes. The input decoder 188 functions to remove the effect of the feedback from the output actuators. Thus, the output of the decoder is substantially the noise signal with the output signal removed. This substantially pure noise signal is then inverted, equalized, amplified and output to the power amplifiers which drive the output actuators. As in the system of FIG. 4, the delayed cancellation circuit functions to remove feedback that appears a system time delay later. Decoding of the input in the presence of a first or a second delayed cancellation signal that was fed back to the input requires that the delayed output be subtracted from each input signal sample. In addition, calculation of the linearity table in the presence of a first or a second delayed cancellation signal also requires that the delayed output be subtracted from each input signal sample.

Another difference from the system of FIG. 4 is that the digital data is output from the digital low pass filter 180 to the input decoder 188 via the multiplier 186. The input decoder 188 functions to discern the interference noise signal from the input signal which includes a feedback signal having a relatively large amplitude. The input decoder comprises a Σ generator similar to the Σ generator 183 of the non linearity correction circuit and which is described in more detail below with reference to the flow diagram of FIG. 13. Note that the high level flow diagrams describing the method of linearity table calibration describe the calibration of a single coefficient. These method are repeated in order to calibrate all the coefficients.

Figure 12:
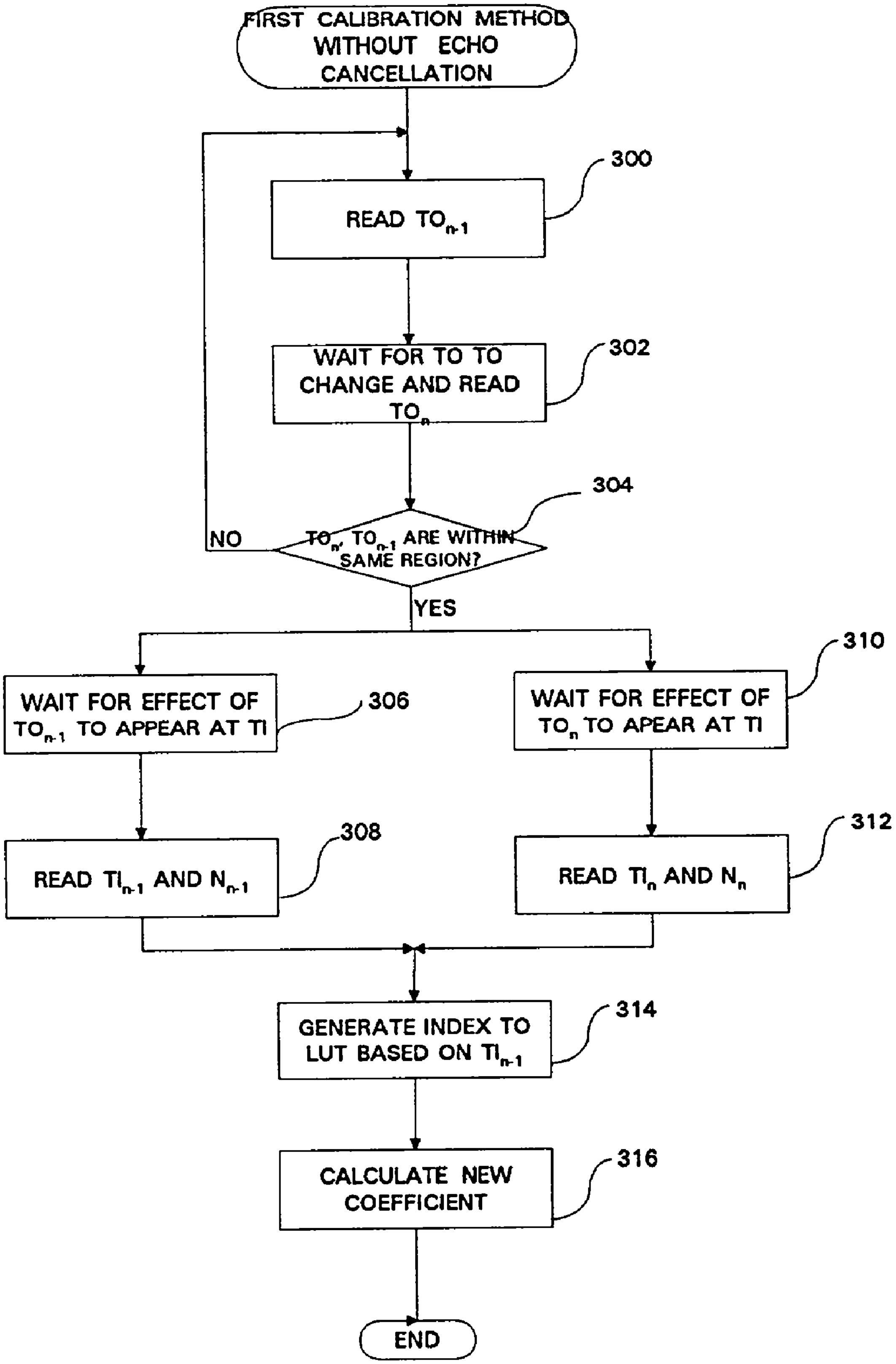
FIG. 12 is a flow diagram illustrating the first calibration method associated with the second embodiment of the present invention.

A high level flow diagram illustrating the first calibration method associated with the second embodiment is shown in FIG. 12. The first method of calibration utilizes the fact that the noise is physical and continuous. The controller in the system tracks the relationship between values termed Table Input (TI), Table Output (TO) and sigma (Σ) during operation of the system. The TI values are measured at the input to the LUT 184. The TO values are measured at the output of the multiplier 186. The Σ values are generated by the Σ generator 183. The coefficient processor functions to calculate new LUT coefficients based on the TI, TO and Σ values.

The calibration of the LUT coefficients during operation of the system attempts to ignore the effects of the noise source. Note that the input noise source itself changes between two adjacent samples. The calibration method measures two adjacent TO values at the output of the multiplier 93 (FIG. 11). Subsequently, the controller then measures two adjacent TI values that are based on the previously measured TO values, assuming the system delay is known. The signal fed back from the output actuator to the input transducer is removed from the TI value to yield an input value that reflects the noise level only. Subsequently, the effect of the noise source is removed from the TI value.

Figure 13:
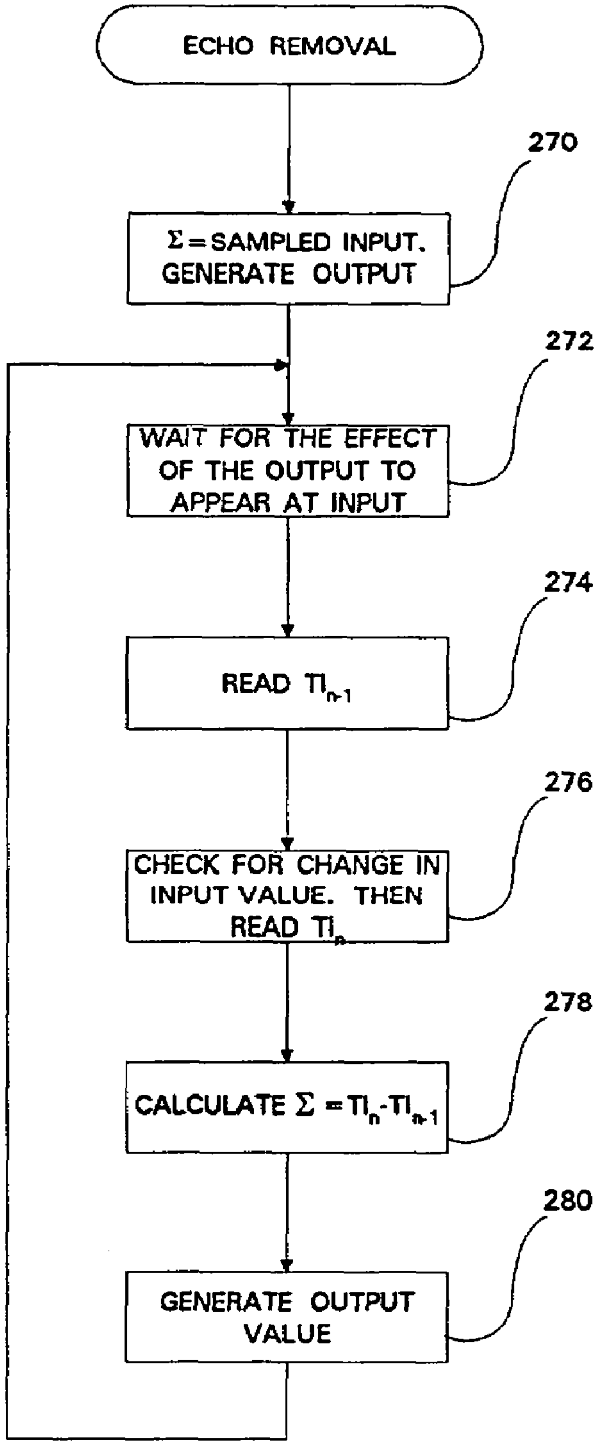
FIG. 13 is a flow diagram illustrating the echo removal method of the present invention utilized in the second embodiment.

To aid in understanding the calibration method described herein, the method of removing feedback signals from the input signal implemented by the Σ generator 183 will first be described in more detail. A high level flow diagram illustrating the echo removal method of the present invention utilized in the second embodiment of the noise reduction system is shown in FIG. 13. It is assumed that the initial speaker output is equal to zero and that the initial Σ is equal to zero. The first step is to sample the input value and set Σ to be equal to the input value in order to drive the output actuator 202 (FIG. 11) (step 270). Next, the system waits for the effect of the output value to appear at the output of the LPF 180, i.e., the Table Input (TI) value, (step 272). The time needed for the output to propagate round trip is termed the system delay time. The system delay time must be known and is typically measured at the time the system is installed after it is first powered on.

Once the effect of the output value appears at the TI, the input value is read and denoted $TI_{n-1}$ (274). This input value, however, reflects both the noise level and the output that was fed back through the input. The system then starts examining input samples in order to detect a change in the input value. When a change is detected, a second input value is read and denoted $TI_n$ (step 276). The delta Δ between the two input values is then calculated and added to a running sum Σ (step 278). The Σ value is then amplified in order to drive the actuator (step 280). The sum is initialized to zero at system startup time and is updated for each change in the input value. The running sum can be expressed as the following.

$$\Delta = TI_n - TI_{n-1}$$

$$\Sigma = \Sigma + \Delta$$

These calculations are performed each time there is a change in TI except during the period within a system delay and one clock period after system delay, as shown in the Table 1 below. As an alternative, the above calculations may be performed once every system clock except during the period that is during the system delay and one clock after system delay, as shown in Table 1 below, regardless of the resulting value of Δ. Note that the value of Δ may often be zero due to the slowly varying input signal relative to the sampling frequency of the A/D converter.

The following table is presented to illustrate the method of FIG. 13.

TABLE I

| System Operation Period | 1 | system delay | 2 | 3 | 4 | 5 | system delay | 6 | 7 | 8 | system delay | 9 | 10 | system delay | 11 |
|---|---|---|---|---|---|---|---|---|---|---|---|---|---|---|---|
| Noise Input | 1 | | 1 | 1 | 1 | 2 | | 2 | 2 | 3 | | 3 | 2 | | 2 |
| Total Measured Input (TI) | 1 ($TI_1$) | | 11 ($TI_2$) | 11 ($TI_3$) | 11 ($TI_4$) | 12 ($TI_5$) | | 22 ($TI_6$) | 22 ($TI_7$) | 23 ($TI_8$) | | 33 ($TI_9$) | 32 ($TI_{10}$) | | 32 ($TI_{11}$) |
| Δ | none | | | | | | | | | 1 | | | −1 | | |
| Σ | 1 | 1 | 1 | 1 | 1 | 2 | 2 | 2 | 2 | 3 | 3 | 3 | 2 | 2 | 2 |
| Speaker Output Reflected to the Input | 0 | | 10 | 10 | 10 | 10 | | 20 | 20 | 20 | | 30 | 30 | | 20 |
| Δ Calculation Detect Change in Input Value | X | | X | | | $TI_5 - TI_2$ * | | X | | $TI_8 - TI_6$ * | | X | $TI_{10} - TI_9$ * | | X |

The following notes will aid in understanding the contents of Table 1 presented above.

1. Note that in system operation period 1 $TI_{n-1}$ has no value, thus according to the equation given above, Δ and Σ are not defined. In this case, Σ is set equal to the input value.
2. The 'X' in the Δ calculations row means that no Δ calculations are performed in that particular system operation period.
3. The time difference between system operation periods that are not marked with '10 μs delay' is time between samples taken by the A/D converter 178 (FIG. 11). Note that there may be numerous periods between 'system delay' periods, i.e., numerous periods until the noise input value changes.
4. Since the system functions to accumulate errors in measurement accuracy, the Σ accumulator does not accumulate continuously. Periodically, before the error increases above a predetermined value, the system waits until Σ becomes nearly zero at which time it sets the Σ generator to the initial conditions. Thus, regardless of the history, the system starts over from period 1 as shown in Table 1.
5. The contents of Table 1 above are associated with the operations of the Σ generator 183 and the input decoder 188 (FIG. 11). It is preferable to set the operation of the two generators to the initial state as explained in Note 4 at the substantially the same time.

The total measured input is the sum of the noise input and the speaker output. The Δ and Σ values are calculated as given above and the speaker output represents the value output by the output actuator as sensed in the input. In this example, the system is considered to have a gain of 10, thus the speaker output, as fed back to the input, is taken as 10 times the value of Σ. As can be seen from Table 1 above, the method effectively removes the effect of the speaker output from the input data.

With reference to FIGS. 11 and 12, the first step in the calibration method is to read a Table Output (TO) value at the output of the multiplier 182, termed $TO_{n-1}$ (step 300). After reading the $TO_{n-1}$ value, the system waits for the difference between $TO_{n-1}$ and $TO_n$ at the output of the multiplier to reach a predetermined minimum before reading the next TO value which is termed $TO_n$ (step 302). This minimum determines the accuracy of the coefficient calibration.

It is then determined whether $TO_n$ is within the same region of the LUT as $TO_{n-1}$ (step 304). This is checked in order to prevent two TO values being associated with different regions of the LUT. The calibration method calculates new coefficients for a single region of the LUT at a time. The calculations, thus, cannot span borders between regions.

Next, the system waits for the effect of the $TO_{n-1}$ value (step 306) and $TO_n$ value (step 310) to appear at the output of the LPF. The data output by the LPF is termed Table Input (TI) data. Once the effect of the $TO_{n-1}$ data appears at the output of the LPF, the $TI_{n-1}$ value is read along with the value of the noise denoted $N_{n-1}$ (step 308). N is the net noise extracted from the echo removal method described hereinabove and is equal to the $\Sigma$ at that particular point in time. Similarly, once the effect of the $TO_n$ data appears at the output of the LPF, the $TI_n$ value is read along with the value of the noise denoted $N_n$ (step 312). The steps of first waiting and then reading the TI values described above can be implemented either sequentially or in parallel.

The $TI_{n-1}$ value is then used to generate an index into the LUT (step 314). The LUT has less entries in it than the number of possible input values, e.g., 256 regions for 12 bits of input data in order to reduce the size of the LUT. Alternatively, the LUT can be constructed to hold a coefficient value for each and every possible input data.

Once the TI and N data have been read, the new coefficient is calculated using the following equation.

$$C_{new} = C_{old} + K\left\{\left[\frac{TO_n - TO_{n-1}}{(TI_n - \Sigma_n) - (TI_{n-1} - \Sigma_{n-1})}\right] - C_{old}\right\}$$

The new coefficient $C_{new}$ is a function of the old coefficient $C_{old}$. The values TO, TI and $\Sigma$ are used to generate an intermediate new coefficient from which the old coefficient $C_{old}$ is subtracted. A portion of the delta (determined by the constant K) is added to $C_{old}$ to perform the calibration. The constant K varies between 0 and 1 and is used to determine the speed with which the coefficients are permitted to change. Values of K closer to 0 cause the coefficients to change more slowly whereas values of K closer to 1 cause the coefficients to change more quickly.

Figure 14:
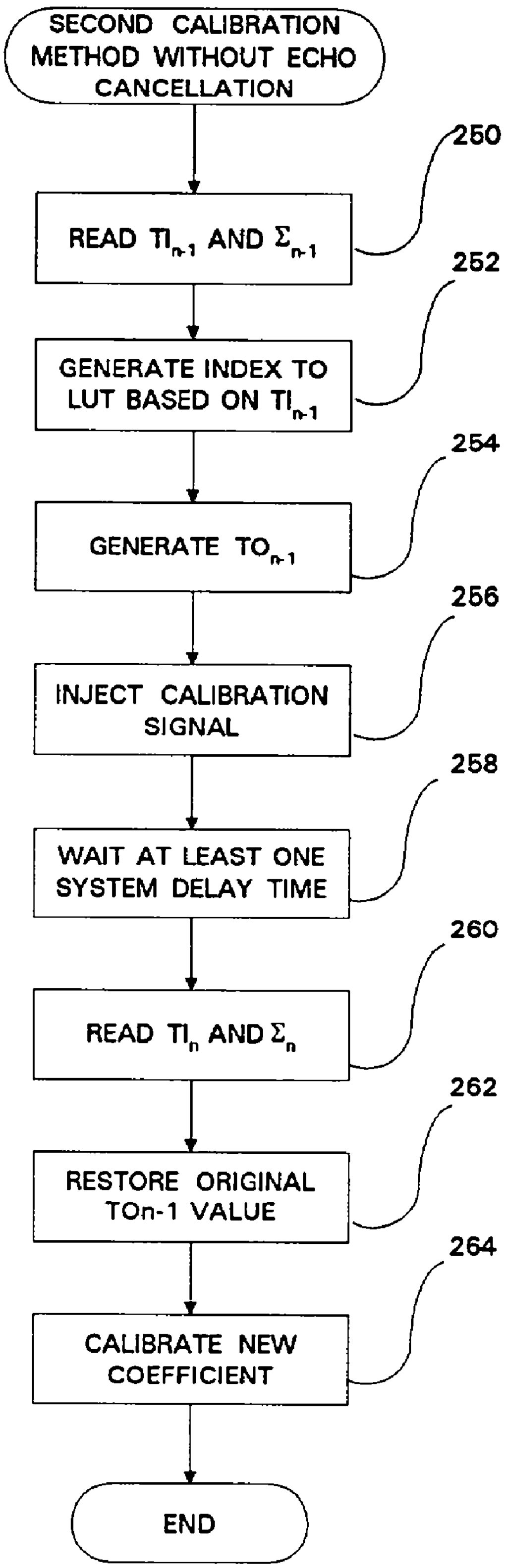
FIG. 14 is a flow diagram illustrating the second calibration method associated with the second embodiment of the present invention.

The second calibration method associated with the first noise reduction embodiment of FIG. 4 will now be described in more detail. A high level flow diagram illustrating the second calibration method associated with the second embodiment of the present invention is shown in FIG. 14. This second method of calibration is similar to that of the first method described in connection with FIG. 12, with the difference being that rather than wait for the actual noise source to cause a change to the TO value, an artificial noise signal is injected into the data path to simulate a known change in the noise signal level. The method utilizes the output of the LPF 180 (TI values), the output of the multiplier 186 (TO values) and the output of the $\Sigma$ generator 183 ($\Sigma$ values) in performing the calibration calculations. The second method of coefficient calibration is performed very quickly relative to the frequency of the input noise. In addition, it is assumed that the smallest period of the input noise is small enough relative to the time delay of the system that it can be regarded as a DC level. This pseudo DC level of the noise is used to point to a particular region in the linearity LUT.

With reference to FIGS. 11 and 14, the first step is to measure the Table Input (TI) value denoted $TI_{n-1}$ at the output of the LPF. The output of the $\Sigma$ generator is also calculated and denoted $\Sigma_{n-1}$ (step 250). The index to the linearity LUT is then generated based on the $TI_{n-1}$ value just measured (step 252). The index determines which of the coefficients of the linearity LUT is to be calibrated during this particular invocation of the method. The next step is to read the Table Output (TO) value, denoted $TO_{n-1}$, at the output of the multiplier 186 (step 254). The TO value is generated by multiplying the output of the LPF with the output of the LUT. The result of the multiplication is input to the input decoder. Note that the TO value is read immediately after the TI value is read without waiting a system time delay.

A calibration signal is then injected at the output of the multiplier (step 256). The output of the multiplier which is denoted as the TO value is replaced with the calibration signal for a finite time period. The calibration signal, termed $TO_n$, comprises the original output of the multiplier $TO_{n-1}$ increased by a known delta amount. The system then waits one system delay time for the injected calibration signal to appear at the output of the LPF (step 258). After waiting one system time delay, the data at the output of the LPF is read and termed $TI_n$. In addition, the output of the $\Sigma$ generator 183 is read and termed $\Sigma_n$ (step 260).

After reading the $TI_n$ value, the original output of the multiplier $TO_{n-1}$ before the calibration signal was injected is restored (step 262). Then, based on the values TI, TO and $\Sigma$, the new coefficient is calculated utilizing the following equation (step 264).

$$C_{new} = C_{old} + K\left\{\left[\frac{TO_n - TO_{n-1}}{(TI_n - \Sigma_n) - (TI_{n-1} - \Sigma_{n-1})}\right] - C_{old}\right\}$$

The new coefficient $C_{new}$ is a function of the old coefficient $C_{old}$. The values TO, TI and $\Sigma$ are used to generate an intermediate new coefficient from which $C_{old}$ is subtracted. A portion of the delta is added to $C_{old}$ to perform the calibration. The constant K varies between 0 and 1 and is used to determine the speed with which the coefficients are permitted to change. Values of K closer to 0 cause the coefficients to change more slowly whereas values of K closer to 1 cause the coefficients to change more quickly.

Note that since the calibration calculation for each coefficient occurs very quickly, the input noise source can be regarded as constant or a pseudo DC value at the time the TI values are measured. Thus, the $\Sigma_{n-1}$ and $\Sigma_n$ values will cancel and thus can be removed from the equation.

While the invention has been described with respect to a limited number of embodiments, it will be appreciated that many variations, modifications and other applications of the invention may be made.

What is claimed is:

1. An acoustic noise reduction system for reducing the effects of a noise source, comprising:

input transducer means for sensing the acoustic noise field generated by the noise source and for generating an input signal therefrom;

output actuator means for generating an acoustic output field that is effective to reduce the level of the acoustic noise field;

correction means for adjusting the input signal generated by said input transducer to compensate for the non linear characteristics of said input transducer and output actuator;

echo cancellation means for removing from the input signal a portion of the output of said output actuator means fed back through said input transducer means, the output of said echo cancellation means representing a signal corresponding to substantially the noise source by itself; and antinoise means for generating an antinoise signal opposite in phase to said input signal, said output actuator means generating said acoustic output field from said antinoise signal, wherein said input transducer means is located in relatively close proximity to said output actuator means, and wherein said antinoise means comprises:

a variable gain amplifier operative to generate an amplified signal 180 degrees opposite in phase from said input signal; and gain control means for dynamically controlling the gain of said variable gain amplifier, wherein said gain control means is adapted to receive a manual input control signal from a user which determines the gain of said variable gain amplifier, said user able to vary the location of a quiet zone generated by said system by varying said input control signal.

2. The system according to claim 1, wherein said input control signal is generated by said user remotely from said system and transmitted to said system via wireless communication means.

3. An acoustic noise reduction system for reducing the effects of a noise source, comprising:

input transducer means for sensing the acoustic noise field generated by the noise source and for generating an input signal therefrom;

output actuator means for generating an acoustic output field that is effective to reduce the level of the acoustic noise field;

correction means for adjusting the input signal generated by said input transducer to compensate for the non linear characteristics of said input transducer and output actuator;

echo cancellation means for removing from the input signal a portion of the output of said output actuator means fed back through said input transducer means, the output of said echo cancellation means representing a signal corresponding to substantially the noise source by itself;

antinoise means for generating an antinoise signal opposite in phase to said input signal, said output actuator means generating said acoustic output field from said antinoise signal; and delay cancellation means for reducing the effect of echo signals caused by said antinoise means sensed by said input transducer, wherein said delay cancellation means comprises a digital filter whose output is added to the output of said antinoise means, wherein said input transducer means is located in relatively close proximity to said output actuator means.

4. An acoustic noise reduction system for reducing the effects of a noise source, comprising:

input transducer means for sensing the acoustic noise field generated by the noise source and for generating an input signal therefrom;

output actuator means for generating an acoustic output field that is effective to reduce the level of the acoustic noise field;

correction means for adjusting the input signal generated by said input transducer to compensate for the non linear characteristics of said input transducer and output actuator;

echo cancellation means for removing from the input signal a portion of the output of said output actuator means fed back through said input transducer means, the output of said echo cancellation means representing a signal corresponding to substantially the noise source by itself;

antinoise means for generating an antinoise signal opposite in phase to said input signal, said output actuator means generating said acoustic output field from said antinoise signal; and delay cancellation means for reducing the effect of echo signals caused by said antinoise means sensed by said input transducer, wherein said delay cancellation means comprises a digital filter whose output is added to the output of said antinoise means, wherein said digital filter comprises a finite impulse response (FIR) digital filter, and wherein said input transducer means is located in relatively close proximity to said output actuator means.

* * * * *